US008569268B2

(12) United States Patent
Holowka

(10) Patent No.: US 8,569,268 B2
(45) Date of Patent: Oct. 29, 2013

(54) ACRYLATE/METHACRYLATE-BASED DIBLOCK COPOLYMER/ANTHRANILIC DIAMIDE COMPOSITIONS FOR PROPAGULE COATING

(75) Inventor: Eric P. Holowka, Philadelphia, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/234,177

(22) Filed: Sep. 16, 2011

(65) Prior Publication Data

US 2012/0149566 A1 Jun. 14, 2012

Related U.S. Application Data

(60) Provisional application No. 61/422,265, filed on Dec. 13, 2010.

(51) Int. Cl.

| | |
|---|---|
| ***A01N 25/26*** | (2006.01) |
| ***A01N 43/48*** | (2006.01) |
| ***A01N 43/40*** | (2006.01) |
| ***A61K 31/44*** | (2006.01) |
| ***A01N 25/00*** | (2006.01) |

(52) U.S. Cl.
USPC ............ 514/100; 504/253; 504/333; 504/405

(58) Field of Classification Search
None
See application file for complete search history.

(56) References Cited

U.S. PATENT DOCUMENTS

| | | | |
|---|---|---|---|
| 5,527,760 A | 6/1996 | Rensing et al. | |
| 5,710,268 A | 1/1998 | Wimmer | |
| 6,202,345 B1 | 3/2001 | Wokal | |
| 6,747,047 B2 | 6/2004 | Lahm et al. | |
| 7,247,647 B2 | 7/2007 | Hughes et al. | |
| 7,696,232 B2 * | 4/2010 | Berger et al. | 514/341 |
| 2012/0149563 A1 | 6/2012 | Tam et al. | |
| 2012/0149564 A1 | 6/2012 | Tam | |
| 2012/0149565 A1 | 6/2012 | Tam | |
| 2012/0149567 A1 | 6/2012 | Holowka | |

FOREIGN PATENT DOCUMENTS

| | | | |
|---|---|---|---|
| CN | 101607940 | | 12/2009 |
| WO | 03/015518 | | 2/2003 |
| WO | 03/015519 | | 2/2003 |
| WO | 03/024222 | | 3/2003 |
| WO | WO 03024222 | * | 3/2003 |
| WO | 2004/027042 | | 1/2004 |
| WO | 2004067528 | | 8/2004 |
| WO | 2006/062978 | | 6/2006 |
| WO | 2008/069990 | | 6/2008 |
| WO | 2009/002856 | | 12/2008 |
| WO | WO 2009/002856 | * | 12/2008 |
| WO | WO-2011049233 | * | 4/2011 |

OTHER PUBLICATIONS

U.S. Appl. No. 13/234,174, Nonfinal Office Action, Jun. 1, 2012.
U.S. Appl. No. 13/234,176, Dated May 30, 2012.
U.S. Appl. No. 13/234,171, Dated May 24, 2012.
U.S. Appl. No. 13/234,179, Dated May 24, 2012.
Tetsumi et al., Amorphous Water-Soluble Cyclodextrin Derivatives . . . , Pharmaceutical Research, vol. 5., No. 11, 1988.
Ben et al., Application of NMR for the Determination of HLB Values of Nonionic Surfactants, Journal of The American Oil Chemists' Society, 1972, vol. 49(8), pp. 499-500.
Guo et al., Calculation of Hydrophile-Lipophile Balance for Polyethoxylated Surfactants by Group Contribution Method, Journal of Colloid and Interface Science, 2006, 298, pp. 441-450.
Pitha et al., Amorphous Water-Soluble Derivatives of Cyclodextrins: Nontoxic Dissolution Enhancing Excipients, 1985, vol. 74 (9), pp. 987-990.
Trapani et al., Determination of Hydrophile-Lipophile Balance of Some Polyethoxylated Non-Ionic Surfactants by Reversed-Phase Thin Layer Chromatography, International Journal of Pharmaceutics, 1995, vol. 116, pp. 95-99.
Berger et al., Apparent and Real Distribution in GPC, Separation Science, 1971, 6(2), pp. 297-303.
Griffin, Classification of Surface-Active Agents by HLB, J. Soc Cosmet, 1949, 1, pp. 311-326.
Nelson et al., Small-Angle Neutron Scattering Study of Adsorbed Pluronic Tri-Block Copolymers on Laponite, Langmuir, 2005, vol. 21, pp. 9176-9182.

* cited by examiner

*Primary Examiner* — Alton Pryor

(57) ABSTRACT

Disclosed is an insecticidal composition comprising by weight based on the total weight of the composition:

(a) from about 9 to about 91% of one or more anthranilic diamide insecticides; and
(b) from about 9 to about 91% of an acrylate/methacrylate-based diblock copolymer component having a water solubility of at least about 5% by weight at 20° C., a hydrophilic-lipophilic balance value of at least about 3, and an average molecular weight ranging from about 1,500 to about 50,000 daltons;

wherein the ratio of component (b) to component (a) is about 1:10 to about 10:1 by weight.

Also disclosed is a geotropic propagule coated with the insecticidal composition. Further disclosed is a liquid composition comprising the insecticidal composition, and a method for protecting a geotropic propagule and plant derived therefrom from a phytophagous insect pest.

13 Claims, No Drawings

ACRYLATE/METHACRYLATE-BASED DIBLOCK COPOLYMER/ANTHRANILIC DIAMIDE COMPOSITIONS FOR PROPAGULE COATING

CROSS-REFERENCE TO RELATED APPLICATIONS

This application claims the benefit of the U.S. Provisional Application No. 61/422,265, filed on Dec. 13, 2010.

FIELD OF THE INVENTION

This invention relates to compositions comprising anthranilic diamide insecticides and acrylate/methacrylate-based diblock copolymers. This invention also relates to geotropic propagules coated with these compositions and to protecting propagules and derived plants from phytophagous insect pests by contacting the propagules with these compositions.

BACKGROUND

Damage by phytophagous insect pests to geotropic propagules such as seeds, rhizomes, tubers, bulbs or corms, and plants derived therefrom causes significant economic losses.

Anthranilic diamides, alternatively called anthranilamides, are a recently discovered class of insecticides having activity against numerous insect pests of economic importance. PCT Publication WO 03/024222 discloses treatment with anthranilic diamides being useful for protecting propagules from phytophagous invertebrate pests. Furthermore, because of the ability of anthranilic diamides to translocate within plants, not only the propagules, but also new growth developing from the propagules can be protected.

Although anthranilic diamides have properties making them suitable for protecting propagules and developing growth, achieving sufficient absorption of anthranilic diamides into the propagule and developing roots to cause insecticidally effective concentrations in parts of the developing plant for which protection is desired can be problematical. Although anthranilic diamide coatings on propagules are exposed to moisture from the propagules and surrounding plant growing medium (e.g., soil), the low water solubility of anthranilic diamide insecticides impedes their mobilization through moisture. Also, until the anthranilic diamides are absorbed into the propagules and developing roots, they are vulnerable to absorption and dissipation through the growing medium.

Achieving insecticidally effective concentrations of anthranilic diamides in foliage by treating propagules requires greater amounts of anthranilic diamides to be available for transport greater distances within the plant. Because the rapidly expanding volume of plant tissue in growing foliage inherently dilutes anthranilic diamide concentrations, absorption of increased amounts of anthranilic diamides is required for protection of foliage, particularly if protection of foliage beyond the first couple leaves and during a substantial part of the growing season is desired.

Accordingly, need exists for new compositions promoting the absorption of anthranilic diamide insecticides into propagules and developing roots. Such compositions have now been discovered.

SUMMARY

One aspect of the present invention is an insecticidal composition comprising by weight based on the total weight of the composition:

(a) from about 9 to about 91% of one or more anthranilic diamide insecticides; and (b) from about 9 to about 91% of an acrylate/methacrylate-based diblock copolymer component having a water solubility of at least about 5% by weight at 20° C., a hydrophilic-lipophilic balance value of at least about 3, and an average molecular weight ranging from about 1,500 to about 50,000 daltons;

wherein the ratio of component (b) to component (a) is about 1:10 to about 10:1 by weight.

Another aspect of the present invention is a geotropic propagule coated with an insecticidally effective amount of the aforedescribed composition.

Another aspect of the present invention is a liquid composition consisting of about 5 to 80 weight % of the aforedescribed composition and about 20 to 95 weight % of a volatile aqueous liquid carrier.

Another aspect of the present invention is a method for protecting a geotropic propagule and plant derived therefrom from a phytophagous insect pest, the method comprising coating the propagule with an insecticidally effective amount of the aforedescribed liquid composition and then evaporating the volatile aqueous liquid carrier of the composition.

DETAILED DESCRIPTION

As used herein, the terms "comprises," "comprising," "includes," "including," "has," "having," "contains," "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of."

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), or both A and B are true (or present).

Also, the indefinite articles "a" and "an" preceding an element or component of the invention are intended to be nonrestrictive regarding the number of instances (i.e., occurrences) of the element or component. Therefore "a" or "an" should be read to include one or at least one, and the singular word form of the element or component also includes the plural unless the number is obviously meant to be singular.

As referred to in the present disclosure and claims, the term "propagule" means a seed or a regenerable plant part. The term "regenerable plant part" means a part of a plant other than a seed from which a whole plant may be grown or regenerated when the plant part is placed in horticultural or agricultural growing media such as moistened soil, peat moss, sand, vermiculite, perlite, rock wool, fiberglass, coconut husk fiber, tree fern fiber and the like, or even a completely liquid medium such as water. The term "geotropic propagule" means a seed or a regenerable plant part obtained from the portion of a plant ordinarily disposed below the surface of the growing medium. Geotropic regenerable plant parts include viable divisions of rhizomes, tubers, bulbs and corms which retain meristematic tissue, such as an eye. Regenerable plant parts such as cut or separated stems and leaves derived from the foliage of a plant are not geotropic and thus are not considered geotropic propagules. As referred to in the present disclosure and claims, unless otherwise indicated, the term "seed" specifically refers to unsprouted seeds. The term "foliage" refers to parts of a plant exposed above ground. Therefore foliage includes leaves, stems, branches, flowers, fruits and buds.

In the context of the present disclosure and claims, protection of a seed or plant grown therefrom from a phytophagous insect pest means protection of the seed or plant from injury or damage potentially caused by the insect pest. This protection is achieved through control of the insect pest. Control of an insect pest can include killing the insect pest, interfering with its growth, development or reproduction, and/or inhibiting its feeding. In the present disclosure and claims the terms "insecticidal" and "insecticidally" relate to any form of insect control.

The terms "suspension concentrate" and "suspension concentrate composition" refer to compositions comprising finely divided solid particles of an active ingredient dispersed in a continuous liquid phase. Said particles retain identity and can be physically separated from the continuous liquid phase. The viscosity of the continuous liquid phase can vary from low to high, and indeed can be so high as to cause the suspension concentrate composition to have a gel-like or paste-like consistency.

The term "particle size" refers to the equivalent spherical diameter of a particle, i.e., the diameter of a sphere enclosing the same volume as the particle. "Median particle size" is the particle size corresponding to half of the particles being larger than the median particle size and half being smaller. With reference to particle size distribution, percentages of particles are also on a volume basis (e.g., "at least 95% of the particles are less than about 10 microns" means that at least 95% of the aggregate volume of particles consists of particles having equivalent spherical diameters of less than about 10 microns). The principles of particle size analysis are well-known to those skilled in the art; for a technical paper providing a summary, see A. Rawle, "Basic Principles of Particle Size Analysis" (document MRK034 published by Malvern Instruments Ltd., Malvern, Worcestershire, UK). Volume distributions of particles in powders can be conveniently measured by such techniques as Low Angle Laser Light Scattering (also known as LALLS and Laser Diffraction), which relies on the fact that diffraction angle is inversely proportional to particle size.

In the recitations herein, the term "alkyl" used either alone or in compound words such as "haloalkyl" or "fluoroalkyl" includes straight-chain or branched alkyl, such as methyl, ethyl, n-propyl, i-propyl, or the different butyl isomers. "Alkoxy" includes, for example, methoxy, ethoxy, n-propyloxy, isopropyloxy and the different butoxy isomers. The term "halogen," either alone or in compound words such as "haloalkyl," includes fluorine, chlorine, bromine or iodine. Further, when used in compound words such as "haloalkyl" or "haloalkoxy," said alkyl may be partially or fully substituted with halogen atoms which may be the same or different. Examples of "haloalkyl" include $CF_3$, $CH_2Cl$, $CH_2CF_3$ and $CCl_2CF_3$. The terms "haloalkoxy," and the like, are defined analogously to the term "haloalkyl." Examples of "haloalkoxy" include $OCF_3$, $OCH_2CCl_3$, $OCH_2CH_2CHF_2$ and $OCH_2CF_3$.

The total number of carbon atoms in a substituent group is indicated by the "$C_i$-$C_j$" prefix where i and j are numbers from 1 to 4. For example, $C_1$-$C_4$ alkyl designates methyl through butyl, including the various isomers.

The present invention relates to the protection of a geotropic propagule and plant derived therefrom from a phytophagous insect pest by coating the propagule with an insecticidally effective amount of an insecticidal composition comprising by weight based on the total weight of the composition:

(a) from about 9 to about 91% of one or more anthranilic diamide insecticides; and (b) from about 9 to about 91% of an acrylate/methacrylate-based diblock copolymer component having a water solubility of at least about 5% by weight at 20° C., a hydrophilic-lipophilic balance value of at least about 3, and an average molecular weight ranging from about 1,500 to about 50,000 daltons;

wherein the ratio of component (b) to component (a) is about 1:10 to about 10:1 by weight.

In some embodiments, the inclusion in the composition of present invention of at least about 9% by weight and in a ratio of at least about 1:10 relative to component (a) of an acrylate/methacrylate-based copolymer having the above described water solubility, HLB value, and average molecular weight has been discovered to promote the absorption of the component (a) active ingredient into the propagule when the composition is coated on a propagule either directly or through the emerging roots, thereby providing more uptake of anthranilic diamide insecticides into the developing plant, including emerging foliage. Increasing uptake of anthranilic diamide insecticides provides insecticidally effective concentrations of the insecticides not only in the propagule, roots, and foliage near ground level but also more distant foliage of the growing plant.

Anthranilic diamide insecticides, also known as anthranilamide insecticides, are members of a class of insecticidal compounds characterized chemically by molecular structures comprising vicinal carboxamide substituents bonded to the carbon atoms of an aryl ring, typically phenyl, wherein one carboxamide moiety is bonded through the carbonyl carbon and the other carboxamide moiety is bonded through the nitrogen atom and characterized biologically by binding to ryanodine receptors in insect muscle cells, causing the channel to open and release calcium ions into the cytoplasm. Depletion of calcium ion stores results in insect paralysis and death. PCT Publication WO 2004/027042 describes an assay for ryanodine receptor ligands. Illustrative of anthranilic diamide insecticides are compounds of Formula 1, N-oxides, and salts thereof,

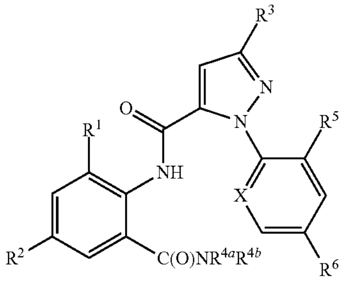

1 wherein

X is N, CF, CCl, CBr or CI;

$R^1$ is $CH_3$, Cl, Br or F;

$R^2$ is H, F, Cl, Br or —CN;

$R^3$ is F, Cl, Br, $C_1$-$C_4$ haloalkyl or $C_1$-$C_4$ haloalkoxy;

$R^{4a}$ is H, $C_1$-$C_4$ alkyl, cyclopropylmethyl or 1-cyclopropylethyl;

$R^{4b}$ is H or $CH_3$;

$R^5$ is H, F, Cl or Br; and $R^6$ is H, F, Cl or Br.

A variety of anthranilic diamide insecticides and methods for their preparation are described in the literature. For example, compounds of Formula 1 and methods for their preparation are reported in U.S. Pat. Nos. 6,747,047 and 7,247,647, and PCT Publications WO 2003/015518, WO 2003/015519, WO 2004/067528, WO2006/062978 and WO2008/069990.

Of particular note for the present compositions and methods of their use are compounds of Formula 1 wherein X is N; $R^1$ is $CH_3$; $R^2$ is Cl or —CN; $R^3$ is Br; $R^{4a}$ is $CH_3$; $R^{4b}$ is H; $R^5$ is Cl; and $R^6$ is H. The compound wherein $R^2$ is Cl has the Chemical Abstracts systematic name 3-bromo-N-[4-chloro-2-methyl-6-[(methylamino)carbonyl]phenyl]-1-(3-chloro-2-pyridinyl)-1H-pyrazole-5-carboxamide and the common name chlorantraniliprole, and is trademarked as an insecticidal active ingredient by DuPont as RYNAXYPYR. The compound wherein $R^2$ is —CN has the Chemical Abstracts systematic name 3-bromo-1-(3-chloro-2-pyridinyl)-N-[4-cyano-2-methyl-6-[(methylamino)carbonyl]phenyl]-1H-pyrazole-5-carboxamide and the proposed common name cyantraniliprole, and is trademarked as an insecticidal active ingredient by DuPont as CYAZYPYR. As disclosed in Example 15 of WO 2006/062978, cyantraniliprole is in the form of solids melting at 177-181° C. or 217-219° C. Both polymorphs are suitable for the present compositions and methods.

Most generally, component (a) is from about 9 to about 91% of the composition by weight. Typically, component (a) is at least about 20%, more typically at least about 30%, and most typically at least 40% of the composition by weight. Component (a) is typically not more than about 80% and more typically not more than about 70% of the composition by weight. To provide optimal biological availability, typically not more than about 30% of component (a), more typically not more than about 20%, and most typically not more than about 10% of component (a) by weight is present in the composition as particles having a particle size greater than about 10 microns. Particle sizes of 10 microns or less can be easily achieved through such techniques as milling.

The term "acrylate/methacrylate-based diblock copolymers" refers to polymers of Formula 2

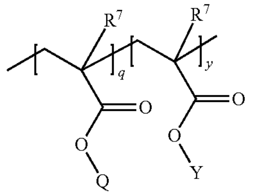

2 where each $R^7$ is independently selected from H and $CH_3$; and q and y are independently selected from integers from 5 to 600.

As shown by the structure depicted in Formula 2, the acrylate/methacrylate-based diblock copolymers are substituted on the carboxyl group with functional groups, Q and Y. Q can be benzyl, glycidyl, $C_1$-$C_{20}$ straight chain alkyl, (e.g., methyl, ethyl, n-butyl, hexadecyl, octadecyl, lauryl, stearyl), $C_3$-$C_{20}$ branched alkyl (e.g., isodecyl, isooctyl, isotridecyl, tert-butyl), 2-phenoxyethyl, isobornyl or tetrahydro furfuryl. Q can also be a functional group derived from the reaction of a glycidyl group with cysteine, tryptophan, dihydroxyphenylalanine, or phenylalanine. Thus, suitable Q groups include functional groups $Q^1$-$Q^9$, shown below:

$Q^1$ = 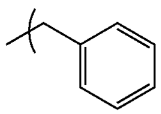 $Q^2$ = 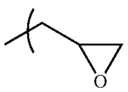

$Q^3$ = 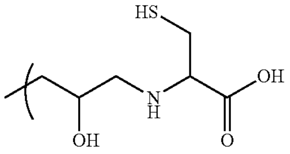

$Q^4$ = 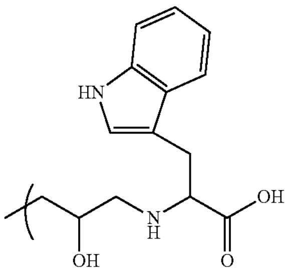

$Q^5$ = 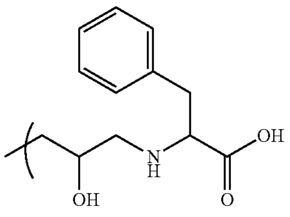

$Q^6$ = 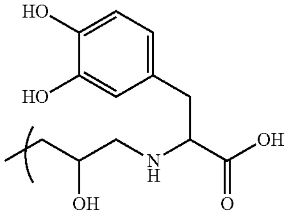

-continued $Q^7$ = 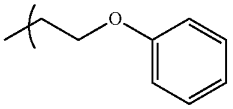 $Q^8$ = 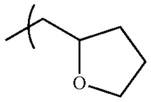

$Q^9$ = 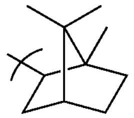

Y can be hydroxyethyl or 3-hydroxy propyl. Y can also be a functional group derived from the reaction of a glycidyl group with lysine, histidine, arginine, asparagine, glutamine, diethylene glycol, triethylene glycol, tetraethylene glycol, or 1,6-hexanediol. Y can also be methoxy ethylene glycol polymers or ethylene glycol polymers with a degree of polymerization of 1 to 113.

Thus, suitable Y groups include the functional groups, $Y^1$-$Y^7$, shown below:

$Y^1$ = 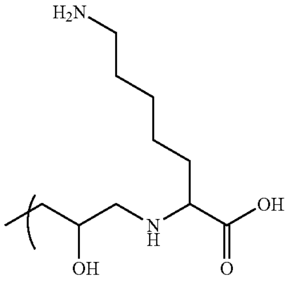

$Y^2$ = 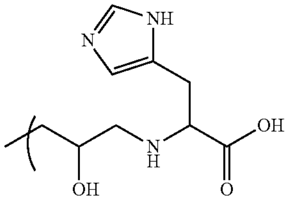

$Y^3$ = 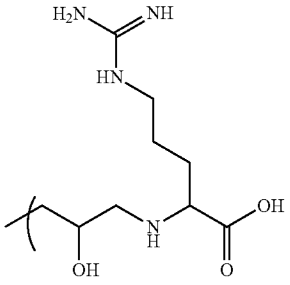

$Y^4$ = 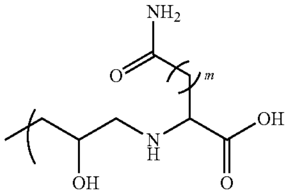

where m = 1, 2

$Y^5$ = 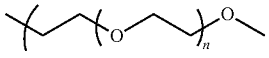

where 1 ≤ n ≤ 113

-continued $Y^6$ = 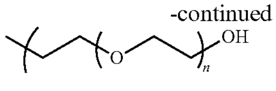 $Y^7$ = 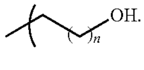

where 1 ≤ n ≤ 113 where 2 ≤ n ≤ 6

Methods for synthesizing diblock acrylate/methacrylate copolymers are well-known in the art. Diblock acrylate/methacrylate copolymers disclosed herein can be synthesized by reacting two or more suitable acrylate/methacrylate monomers in the presence of an appropriate transfer agent or metal catalyst system, and an appropriate initiating species in a suitable solvent. The second monomer is added after the first monomer is fully polymerized.

Suitable acrylate/methacrylate monomers are those which can form secondary or tertiary radical active species and include at least one monomer of Formula 3 and at least one monomer of Formula 4,

3

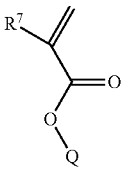

4

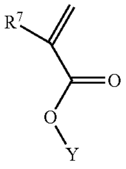

where $R^7$, Q and Y are as defined above.

Suitable transfer agents include: dithiobenzoates, trithiocarbonates, dithiocarbamates, 2-cyano-2-propyl benzodithioate, 4-cyano-4-(phenylcarbonothioylthio)pentanoic acid, 2-cyano-2-propyl dodecyltrithiocarbonate, 4-cyano-4-[(dodecylsulfanylthiocarbonyl)sulfanyl]pentanoic acid, and 2-(dodecylthiocarbonothioylthio)-2-methylpropionic acid.

Suitable metal catalyst systems include: copper (I) bromide/bipyridine; copper (I) bromide/4,4'-dinonyl-2,2'-dipyridyl; copper (I) bromide/N,N,N',N'',N''-pentamethyldiethylenetriamine; copper (I) bromide/tris(2-pyridylmethyl)amine; copper (I) bromide/tris[2-(dimethylamino)ethyl]amine; copper (I) chloride/bipyridine; copper (I) chloride/4,4'-dinonyl-2,2'-dipyridyl; copper (I) chloride/N,N,N',N'',N''-pentamethyldiethylenetriamine; copper (I) chloride/tris(2-pyridylmethyl)amine; and copper (I) chloride/tris[2-(dimethylamino)ethyl]amine.

Suitable initiating species include: ethyl 2-bromoisobutyrate, octadecyl 2-bromoisobutyrate, dodecyl 2-bromoisobutyrate, 2-hydroxyethyl 2-bromoisobutyrate, and 2,2,5-trimethyl-3-(1-phenylethoxy)-4-phenyl-3-azahexane.

Suitable solvents include: tetrahydrofuran, acetone, and ethanol.

The polymerization is typically run in an air-free environment, and all reagents are treated to remove oxygen prior to use. A transfer agent or catalyst species and the initiator species are typically added to a reaction vessel, such that the ratio of transfer agent (or catalyst species) is less than 1:1, relative to the initiator species. The first monomer is then added to the reaction vessel under nitrogen. Once the components are solubilized, the initiating species is added and the reaction mixture is maintained at the desired temperature. After the first monomer is consumed, the second monomer is added. Reactions can be monitored using size-exclusion chromatography to determine completion, which is signified by a molecular weight plateau. Residual transfer agents and/or catalyst species can be removed by conventional means, such as column chromatography. The solvent can be removed, e.g., under vacuum, to provide the desired diblock copolymer.

The acrylate/methacrylate-based diblock copolymer component (b) has an average molecular weight ranging from about 1,500 to about 50,000 daltons. In some embodiments, the average molecular weight of component (b) is at least about 5,000, 15,000, 25,000 or 35,000 daltons. In some embodiments, the average molecular weight of component (b) is not more than about 35,000 or 40,000 daltons.

In the present disclosure and claims, the average molecular weight of the acrylate/methacrylate-based diblock copolymer component is the number average, which corresponds (for a given weight of the component) to multiplying the number of acrylate/methacrylate-based diblock copolymer molecules of each molecular weight by their molecular weight, then adding the multiplication products, and finally dividing the calculated sum by the total number of acrylate/methacrylate-based diblock copolymer molecules. However, other definitions of average molecular weight typically give values of a similar order of magnitude. The average molecular weight of methyl methacrylate-based polymers can be measured by methods known in the art, such as gel permeation chromatography cited by Berger, Schulz, and Guenter Separation Science 1971, 6(2), 297-303. Manufacturers of methoxy ethylene glycol methacrylate monomers that can be used to synthesize the acrylate/methacrylate-based diblock copolymers of this invention generally disclose average molecular weight information, and this information can be used to select acrylate/methacrylate-based diblock copolymers for component (b) of the present composition.

Typically, the molecules forming the acrylate/methacrylate-based diblock copolymer component (i.e., component (b)) do not all have the same molecular weight, but instead molecular weights of the molecules form a distribution (e.g., normal Gaussian). Generally, chemical synthesis processes to prepare acrylate/methacrylate-based diblock copolymers give unimodal distributions of molecular weights. However, component (b) of the present composition can comprise acrylate/methacrylate-based diblock copolymers prepared with polyethylene oxide units of different lengths in a polydisperse form. Therefore, the molecular weight distribution of the methoxy ethylene glycol component of (b) can be bimodal or even multimodal. Typically, at least about 90%, more typically at least about 95% and most typically at least about 98%, of the acrylate/methacrylate-based diblock copolymer molecules forming component (b) have molecular weights not exceeding about 40000 daltons.

Acrylate/methacrylate-based diblock copolymers typically have blocks of acrylate/methacrylate-based units functionalized with Q groups, with an average molecular weight of at least about 2,000 daltons, which corresponds to the average value for the subscript variable "q" in Formula 2 being at least about 20. More typically, the average molecular weight of the blocks of acrylate/methacrylate-based units containing Q groups is greater than 3,000 daltons. Typically, 5 q 600.

In acrylate/methacrylate-based diblock copolymer molecules, the Y group provides the hydrophile, while the Q group provides the hydrophobe (or lipophile). Typically, $5 \le y \le 600$.

Blocks of acrylate/methacrylate-based units containing Q groups are lipophilic, whereas blocks of acrylate/methacrylate-based units containing Y group are hydrophilic. Combination of a block of acrylate/methacrylate-based units containing Q groups with a block of acrylate/methacrylate-based units containing Y groups results in an amphiphilic molecular structure providing surfactant properties. The acrylate/methacrylate-based chain with Y groups, which typically contains functionality equivalent to or resembling $Y^1$ to $Y^7$ functionalities, can be described as the hydrophile. The acrylate/methacrylate-based chain with Q groups, which typically contains functionality equivalent to or resembling $Q^1$ to $Q^9$, can be described as the lipophile. The size and type of acrylate/methacrylate-based units can be selected to achieve the required physical properties (e.g., water solubility, HLB, molecular weight) for this component.

In the present composition, component (b) (i.e., the acrylate/methacrylate-based diblock copolymer component) has a water solubility of at least about 1% by weight at 20° C. Accordingly, component (b) is soluble in water at 20° C. to the extent of at least about 5% (by weight), which means that a saturated solution or liquid crystalline phase of component (b) in water at 20° C. contains at least about 5% by weight of component (b). (For simplicity, water solubility is accordingly defined in the present disclosure as percent by weight even if "by weight" is not expressly stated.) If component (b) contains multiple acrylate/methacrylate-based diblock copolymer constituents, typically each constituent has a water solubility of at least about 5% at 20° C. Most acrylate/methacrylate-based diblock copolymers suitable for component (b) have significantly greater water solubilities (e.g., greater than 10%) and many are miscible with water (e.g., soluble in water in all proportions). Decreased absorption of anthranilic diamide insecticides into a propagule and/or developing roots is observed when water-insoluble acrylate/methacrylate-based diblock copolymers are substituted for acrylate/methacrylate-based diblock copolymers having water solubility of at least about 5% as component (b) in a composition coating a seed in soil.

In the context of the present invention, "water solubility" means that component (b) is capable of being completely dissolved in pure water (i.e., the mixtures consist only of water and component (b)) in the weight percentage amount indicated to form (1) a solution consisting of separate acrylate/methacrylate-based copolymer molecules (commonly referred to as unimers) dispersed in the water phase, and/or acrylate/methacrylate-based copolymer molecules aggregated into micelles (i.e., clusters with hydrophilic components of the molecules forming the exterior and hydrophobic components forming the interior of the clusters) dispersed in the water phase, and/or (2) a lyotropic liquid crystalline phase containing clusters of acrylate/methacrylate-based copolymer molecules aggregated so that hydrophilic components of the molecules form the cluster exterior and hydrophobic components form the cluster interior wherein the clusters are isotropically or anisotropically ordered relative to one another in regards to position and/or orientation in the presence of water. Liquid crystalline phases are often viscous or even gel-like, but nevertheless clear. Anisotropic liquid crystalline phases are generally birefringent, whereas isotropic liquid crystalline phases are not. Although a dispersion of micelles in an aqueous medium is a manifestation of water solubility, dispersions and emulsions of droplets (such as of oils and other water-immiscible liquids) lacking both the exterior and interior order of micelles are not examples of water solubility. Microemulsions of droplets differing from micelles by having interiors consisting of constituents besides the hydrophobic components of acrylate/methacrylate-based diblock copolymer molecules are not examples of solutions or water solubility according to the present definition.

The hydrophilic-lipophilic balance (HLB) of a surfactant is an overall measure of the degree to which it is hydrophilic or lipophilic, and is determined by the ratio of polar and non-polar groups in the surfactant molecule. The HLB number of a surfactant indicates the polarity of the surfactant molecules in an arbitrary range of 1 to 40, wherein the number increases with increasing hydrophilicity. The HLB number for a surfactant can be determined by the "emulsion comparison method" of Griffin (W. C. Griffin, *J. Soc. Cosmet. Chem.* 1949, 1, 311-326). Alternatively, the HLB number can be estimated numerically or predicted by a variety of experimental techniques; see X. Guo et al., *Journal of Colloid and Interface Science* 2006, 298, 441-450; G. Ben-Et and D. Tatarsky, Journal of the American Oil Chemists' Society 1972, 49(8), 499-500; G. Trapani et al., *International Journal of Pharmceutics* 1995, 116, 95-99; and the references cited therein.

The acrylate/methacrylate-based diblock copolymer component (i.e., component (b)) of the present composition has an HLB value of at least about 3. Acrylate/methacrylate-based diblock copolymer components having HLB values less than about 3 typically have limited water solubility, which can be less than 5% at 20° C. Acrylate/methacrylate-based diblock copolymers having HLB values near 1 are generally regarded as insoluble in water. Although acrylate/methacrylate-based diblock copolymer components having HLB values less than about 3 can promote absorption of the component (a) active ingredient into propagules and developing roots, their ability to promote the desired absorption in a soil medium is observed to be significantly less than for components having HLB values of at least about 3. Typically, the HLB value of component (b) is greater than 5, such as 6, 7 or 8. In certain embodiments, the HLB value of component (b) is at least about 10. Embodiments wherein the HLB value of component (b) is at least about 20 are of particular note, because acrylate/methacrylate-based diblock copolymers having HLB values at least about 20 are typically very water soluble (i.e., >25% water solubility at 20° C.). High water solubility facilitates preparing highly concentrated liquid compositions from moderate amounts of water, which reduces the amount of water that needs to be evaporated after coating propagules. Although component (b) having a high HLB value is particularly useful in the present composition, the HLB range is limited to 40. Usually component (b) has a HLB value of not more than about 35. Typically, commercially available acrylate/methacrylate-based diblock copolymers do not have an HLB value of more than about 31. Component (b) can have an HLB value of not more than about 20 or not more than about 15.

The HLB value desired for the acrylate/methacrylate-based diblock copolymer component can be achieved by mixing in the proper ratio two or more acrylate/methacrylate-based diblock copolymers having HLB values above and below the desired HLB value. The HLB value for a combination of surfactants is generally close to the value calculated based on HLB contributions of the constituent surfactants according to their weight percentages. Component (b) can contain an acrylate/methacrylate-based diblock copolymer having an HLB value of less than 3 if component (b) also contains a sufficient amount of one or more other acrylate/methacrylate-based diblock copolymers having HLB values greater than 5, so that the resulting HLB value of component (b) is at least about 3. For example, a mixture of two acrylate/methacrylate-based diblock copolymers having HLB values of 1 and 15 (e.g., 2-D3301 and 2-D337) in a 1:8 ratio by weight has an HLB value greater than 5. Typically, the HLB value of each constituent in a mixture of acrylate/methacrylate-based copolymers forming component (b) is at least about 3.

For acrylate/methacrylate-based diblock copolymers used in component (b), the total molecular weight of the peripheral hydrophile (i.e., Y group) is typically in the range of about 20% to about 90% of the weight of the molecule. A hydrophile content of at least about 20% provides water solubility of at least about 5% at 20° C. A hydrophile content of at least about 60% typically provides high water solubility (i.e., >25% water solubility at 20° C.), which facilitates preparing concentrated aqueous liquid compositions. Although the hydrophile content can be 90% or even higher, more typically the total molecular weight of the hydrophile is not more than about 80% of the weight of the molecule.

The physical consistency of acrylate/methacrylate-based diblock copolymers in their pure form ranges from liquids to viscous solids to solids (typically described as powders) at 20° C. Acrylate/methacrylate-based diblock copolymers having an HLB value of at least about 18 are typically solids at 20° C., while acrylate/methacrylate-based diblock copolymers having lower HLB values are typically liquids or viscous solids depending upon both HLB value and molecular weight (lower HLB and lower molecular weight favoring liquids versus viscous solids). Acrylate/methacrylate-based diblock copolymers that are viscous solids or solids facilitate component (b) functioning as an adhesive to affix the composition to a propagule. Acrylate/methacrylate-based diblock copolymers that are solids are of particular note as constituents of component (b), because they provide durable coatings without needing to include additional adhesives such as film formers in the composition.

The inclusion of both hydrophobic groups (e.g., Q groups as described above) and hydrophilic groups (e.g., Y groups as described above) provides acrylate/methacrylate-based copolymer molecules with an amphiphilic combination of well-defined hydrophilic and lipophilic regions, thereby resulting in the ability to function as a surfactant.

Generally, increasing the weight ratio of component (b) to component (a) increases the absorption of component (a) into the propagule and/or developing roots to protect also the foliage of a plant grown from a propagule coated with a composition comprising components (a) and (b). However, increasing component (b) also reduces the amount of component (a) that can be included in the composition. Generally, the weight ratio of component (b) to component (a) is at least about 1:10, typically at least about 1:8, more typically from at least about 1:5 or 1:4, and most typically at least about 1:3. In some embodiments the weight ratio of component (a) to component (b) is at least about 1:2 or 1:1. Generally, the weight ratio of component (b) to component (a) is not more than about 10:1, typically not more than about 8:1, more typically not more than about 4:1, and most typically not more than about 3:1. In some embodiments the weight ratio of component (a) to component (b) is not more than about 2:1 or 1:1.

Most generally, component (b) is from about 9 to about 91% of the composition by weight. Increasing the amount of component (b) can increase the ratio of component (b) to component (a) to facilitate absorption of component (a) from the propagule coating into the propagule and/or developing roots, but also reduces the concentration of component (a) in the coating and accordingly requires a thicker coating to provide a desired amount of component (a) for each propagule. Typically, component (b) is at least about 15%, more typically at least about 20%, and most typically at least 25% of the composition by weight. In some embodiments, component (b) is at least about 30%, 35% or 40% of the composition by weight. Component (b) is typically not more than about 80%, more typically not more than about 70%, and most typically not more than about 60% of the composition by weight. In some embodiments, component (b) is not more than about 50% or 40% of the composition by weight.

The present composition can optionally further comprise (c) up to about 90% by weight of one or more biologically active agents other than anthranilic diamide insecticides. Biologically active agents of component (c) do not include biocides whose principal effect is to preserve the present composition rather than protect a plant contacted with the present composition.

If present, component (c) is typically at least about 0.1% and more typically at least about 1% of the composition by weight. Typically, component (c) is not more than about 60%, more typically not more than about 50%, 40% or 30%, and most typically not more than about 20% of the composition by weight. The biologically active agents forming component (c) differ from the component (a) anthranilic diamide insecticides and can include chemical compounds or biological organisms selected from the following classes: insecticides, fungicides, nematocides, bactericides, acaricides, herbicides, growth regulators such as rooting stimulants, chemosterilants, semiochemicals, repellents, attractants, pheromones and feeding stimulants (including both chemical and biological agents), and mixtures of several compounds or organisms selected from the above classes.

Compositions comprising different biologically active agents can have a broader spectrum of activity than a single agent alone. Furthermore, such mixtures can exhibit a synergistic effect.

Examples of component (c) (i.e., the one or more biologically active agents other than anthranilic diamide insecticides) include: insecticides such as abamectin, acephate, acequinocyl, acetamiprid, acrinathrin, amidoflumet, amitraz, avermectin, azadirachtin, azinphos-methyl, bifenthrin, bifenazate, bistrifluoron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, amitraz, avermectin, azadirachtin, bifenthrin, buprofezin, cadusafos, carbaryl, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of Nucleo polyhydrosis viruses.

One embodiment of biological agents for mixing with compounds of this invention include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other biologically active agent belongs to a different chemical class or has a different site of action than the compound of Formula 1. In certain instances, a combination with at least one other biologically active agent having a similar spectrum of control but a different site of action will be particularly advantageous for resistance management. Thus, a composition of the present invention can further comprise at least one additional biologically active agent having a similar spectrum of control but belonging to a different chemical class or having a different site of action. These additional biologically active compounds or agents include, but are not limited to, sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (gamma-aminobutyric acid)-gated chloride channel antagonists such as avermectin or blockers such as ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; molting inhibitors and ecdysone agonists such as azadirachtin, methoxyfenozide and tebufenozide; ryanodine receptor ligands such as ryanodine, anthranilic diamides such as chlorantraniliprole, cyantraniliprole and flubendiamide; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin or endosulfan; pyrethroids; carbamates; insecticidal ureas; and biological agents including nucleopolyhedro viruses (NPV), members of *Bacillus thuringiensis*, encapsulated delta-endotoxins of *Bacillus thuringiensis*, and other naturally occurring or genetically modified insecticidal viruses.

Further examples of biologically active compounds or agents with which compounds of this invention can be formulated are: fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of a compound of this invention with other biologically active (particularly invertebrate pest control) compounds or agents (i.e. active ingredients) can result in a greater-than-additive (i.e., synergistic) effect. Reducing the quantity of active ingredients released in the environment while ensuring effective pest control is always desirable. When synergism with biologically active agents occurs at application rates giving agronomically satisfactory levels of insect control, such combinations can be advantageous for reducing crop production cost and decreasing environmental load.

Compounds of this invention and compositions thereof can be applied to plants genetically transformed to express proteins toxic to insect pests (such as *Bacillus thuringiensis* delta-endotoxins). Such an application may provide a broader spectrum of plant protection and be advantageous for resistance management. The effect of the exogenously applied compounds of this invention may be synergistic with the expressed toxin proteins.

General references for these agricultural protectants (i.e., insecticides, fungicides, nematocides, acaricides, herbicides and biological agents) include *The Pesticide Manual, 13th Edition*, C. D. S. Tomlin, Ed., British Crop Protection Council, Farnham, Surrey, U.K., 2003 and *The BioPesticide Manual, $2^{nd}$ Edition*, L. G. Copping, Ed., British Crop Protection Council, Farnham, Surrey, U.K., 2001.

Table A lists specific combinations of a compound of Formula 1 with other biologically active agents illustrative of the mixtures, compositions and methods of the present invention and includes additional embodiments of weight ratio ranges for application rates. The first column of Table A lists the specific insect control agents (e.g., “Abamectin” in the first line). The second column of Table A lists the mode of action (if known) or chemical class of the insect pest control agents. The third column of Table A lists embodiment(s) of ranges of weight ratios for rates at which the insect pest control agent can be applied relative to a compound of Formula 1 (e.g., “50:1 to 1:50” of abamectin relative to a compound of Formula 1 by weight). Thus, for example, the first line of Table A specifically discloses the combination of a compound of Formula 1 with abamectin can be applied in a weight ratio between 50:1 to 1:50. The remaining lines of Table A are to be construed similarly.

TABLE A

| Insect Pest Control Agent | Mode of Action or Chemical Class | Typical Weight Ratio |
|---|---|---|
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyantraniliprole | ryanodine receptor ligands | 100:1 to 1:120 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |

TABLE A-continued

| Insect Pest Control Agent | Mode of Action or Chemical Class | Typical Weight Ratio |
|---|---|---|
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

Of note is the composition of the present invention wherein the at least one additional biologically active compound or agent is selected from the insect pest control agents listed in Table A above.

The weight ratios of a compound of Formula 1, an N-oxide, or a salt thereof, to the additional insect pest control agent typically are between 1,000:1 and 1:1,000, with one embodiment being between 500:1 and 1:500, another embodiment being between 250:1 and 1:200 and another embodiment being between 100:1 and 1:50.

Listed below in Tables B1 and B2 are embodiments of specific compositions comprising a compound of Formula 1

(Compound 1 is 3-bromo-1-(3-chloro-2-pyridinyl)-N-[4-cyano-2-methyl-6-[(methylamino)-carbonyl]phenyl]-1H-pyrazole-5-carboxamide and Compound 2 is 3-bromo-N-[4-chloro-2-methyl-6-[(methylamino)carbonyl]phenyl]-1-(3-chloro-2-pyridinyl)-1H-pyrazole-5-carboxamide) and an additional insect pest control agent.

TABLE B1

| Mixture No. | Cmpd. No. | and | Invertebrate Pest Control Agent |
|---|---|---|---|
| B1-1 | 1 | and | Abamectin |
| B1-2 | 1 | and | Acetamiprid |
| B1-3 | 1 | and | Amitraz |
| B1-4 | 1 | and | Avermectin |
| B1-5 | 1 | and | Azadirachtin |
| B1-5a | 1 | and | Bensultap |
| B1-6 | 1 | and | Beta-cyfluthrin |
| B1-7 | 1 | and | Bifenthrin |
| B1-8 | 1 | and | Buprofezin |
| B1-9 | 1 | and | Cartap |
| B1-10 | 1 | and | Chlorantraniliprole |
| B1-11 | 1 | and | Chlorfenapyr |
| B1-12 | 1 | and | Chlorpyrifos |
| B1-13 | 1 | and | Clothianidin |
| B1-14 | 1 | and | Cyantraniliprole |
| B1-15 | 1 | and | Cyfluthrin |
| B1-16 | 1 | and | Cyhalothrin |
| B1-17 | 1 | and | Cypermethrin |
| B1-18 | 1 | and | Cyromazine |
| B1-19 | 1 | and | Deltamethrin |
| B1-20 | 1 | and | Dieldrin |
| B1-21 | 1 | and | Dinotefuran |
| B1-22 | 1 | and | Diofenolan |
| B1-23 | 1 | and | Emamectin |
| B1-24 | 1 | and | Endosulfan |
| B1-25 | 1 | and | Esfenvalerate |
| B1-26 | 1 | and | Ethiprole |
| B1-27 | 1 | and | Fenothiocarb |
| B1-28 | 1 | and | Fenoxycarb |
| B1-29 | 1 | and | Fenvalerate |
| B1-30 | 1 | and | Fipronil |
| B1-31 | 1 | and | Flonicamid |
| B1-32 | 1 | and | Flubendiamide |
| B1-33 | 11 | and | Flufenoxuron |
| B1-34 | 1 | and | Hexaflumuron |
| B1-35 | 1 | and | Hydramethylnon |
| B1-36 | 1 | and | Imidacloprid |
| B1-37 | 1 | and | Indoxacarb |
| B1-38 | 1 | and | Lambda-cyhalothrin |
| B1-39 | 1 | and | Lufenuron |
| B1-40 | 1 | and | Metaflumizone |
| B1-41 | 1 | and | Methomyl |
| B1-42 | 1 | and | Methoprene |
| B1-43 | 1 | and | Methoxyfenozide |
| B1-44 | 1 | and | Nitenpyram |
| B1-45 | 1 | and | Nithiazine |
| B1-46 | 1 | and | Novaluron |
| B1-47 | 1 | and | Oxamyl |
| B1-48 | 1 | and | Phosmet |
| B1-49 | 1 | and | Pymetrozine |
| B1-50 | 1 | and | Pyrethrin |
| B1-51 | 1 | and | Pyridaben |
| B1-52 | 1 | and | Pyridalyl |
| B1-53 | 1 | and | Pyriproxyfen |
| B1-54 | 1 | and | Ryanodine |
| B1-55 | 1 | and | Spinetoram |
| B1-56 | 1 | and | Spinosad |
| B1-57 | 1 | and | Spirodiclofen |
| B1-58 | 1 | and | Spiromesifen |
| B1-59 | 1 | and | Spirotetramat |
| B1-60 | 1 | and | Tebufenozide |
| B1-61 | 1 | and | Thiacloprid |
| B1-62 | 1 | and | Thiamethoxam |
| B1-63 | 1 | and | Thiodicarb |
| B1-64 | 1 | and | Thiosultap-sodium |
| B1-65 | 1 | and | Tolfenpyrad |
| B1-66 | 1 | and | Tralomethrin |

TABLE B1-continued

| Mixture No. | Cmpd. No. | and | Invertebrate Pest Control Agent |
|---|---|---|---|
| B1-67 | 1 | and | Triazamate |
| B1-68 | 1 | and | Triflumuron |
| B1-69 | 1 | and | *Bacillus thuringiensis* |
| B1-70 | 1 | and | *Bacillus thuringiensis* delta-endotoxin |
| B1-71 | 1 | and | NPV (e.g., Gemstar) |

Table B2

Table B2 is identical to Table B1, except that each reference to Compound 1 in the column headed "Cmpd. No." is replaced by a reference to Compound 2. For example, the first mixture in Table B2 is designated B2-1 and is a mixture of Compound 2 and the additional insect pest control agent abamectin.

The specific mixtures listed in Tables B1 and B2 typically combine a compound of Formula 1 with the other invertebrate pest agent in the ratios specified in Table A.

Listed below in Tables C1 and C2 are embodiments of specific compositions comprising a compound of Formula 1 (Compound 1 is 3-bromo-1-(3-chloro-2-pyridinyl)-N-[4-cyano-2-methyl-6-[(methylamino)-carbonyl]phenyl]-1H-pyrazole-5-carboxamide and Compound 2 is 3-bromo-N-[4-chloro-2-methyl-6-[(methylamino)carbonyl]phenyl]-1-(3-chloro-2-pyridinyl)-1H-pyrazole-5-carboxamide) and an additional fungicide.

TABLE C1

| Mixture No. | Cmpd. No. | and | Fungicide |
|---|---|---|---|
| C1-1 | 1 | and | Probenazole |
| C1-2 | 1 | and | Tiadinil |
| C1-3 | 1 | and | Isotianil |
| C1-4 | 1 | and | Pyroquilon |
| C1-5 | 1 | and | Metominostrobin |
| C1-6 | 1 | and | Flutolanil |
| C1-7 | 1 | and | Validamycin |
| C1-8 | 1 | and | Furametpyr |
| C1-9 | 1 | and | Pencycuron |
| C1-10 | 1 | and | Simeconazole |
| C1-11 | 1 | and | Orysastrobin |
| C1-12 | 1 | and | Trifloxystrobin |
| C1-13 | 1 | and | Isoprothiolane |
| C1-14 | 1 | and | Azoxystrobin |
| C1-15 | 1 | and | Tricyclazole |
| C1-16 | 1 | and | Hexaconazole |
| C1-17 | 1 | and | Difenoconazole |
| C1-18 | 1 | and | Cyproconazole |
| C1-19 | 1 | and | Propiconazole |
| C1-20 | 1 | and | Fenoxanil |
| C1-21 | 1 | and | Ferimzone |
| C1-22 | 1 | and | Fthalide |
| C1-23 | 1 | and | Kasugamycin |
| C1-24 | 1 | and | Picoxystrobin |
| C1-25 | 1 | and | Penthiopyrad |
| C1-26 | 1 | and | Famoxadone |
| C1-27 | 1 | and | Cymoxanil |
| C1-28 | 1 | and | Proquinazid |
| C1-29 | 1 | and | Flusilazole |
| C1-30 | 1 | and | Mancozeb |
| C1-31 | 1 | and | Copper hydroxide |
| C1-32 | 1 | and | (a) |

(a) 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone Table C2

Table C2 is identical to Table C1, except that each reference to Compound 1 in the column headed "Cmpd. No." is replaced by a reference to Compound 2. For example, the first mixture in Table C2 is designated C2-1 and is a mixture of Compound 2 and the additional fungicide probenazole.

As an alternative to including other biologically active agents as component (c) in the present composition, other biologically active ingredients can be separately applied to propagules.

The present composition can optionally further comprise (d) up to about 80% by weight of one or more inert formulating ingredients other than acrylate/methacrylate-based diblock copolymers. As used herein, the term "inert formulating ingredient" refers to ingredients included in compositions other than the chemicals or other agents providing the biological activity to control the intended pests (e.g., as described for component (c)). Such inert formulating ingredients are also known as formulation aids. When present, component (d) is typically at least 0.1% of the composition by weight. Except when the composition is intended for pelleting seeds, the amount of component (d) is typically not more than about 20% of the composition by weight.

Component (d) can comprise a wide variety of inert formulating ingredients other than the acrylate/methacrylate-based diblock copolymers of component (b), including for example, adhesives, liquid diluents, solid diluents, surfactants (e.g., having wetting agent, dispersant and/or anti-foam properties), antifreeze agents, preservatives such as chemical stabilizers or biocides, thickening agents and fertilizers. The acrylate/methacrylate-based diblock copolymers of component (b) can function as surfactants (e.g., wetting agents, dispersants) and/or adhesives. Indeed, acrylate/methacrylate-based diblock copolymers are well-known for their wetting and dispersing properties, although they are generally included in formulations at concentrations substantially less than specified herein. Therefore component (b) can reduce or eliminate the benefit of including certain additional inert formulating ingredients as constituents of component (d). Nevertheless, inclusion of ingredients such as surfactants and adhesives in component (d) may still be desirable.

In the context of the present disclosure and claims, the term "adhesive" refers to a substance capable of binding component (a) to a propagule such as a seed. Adhesives include substances exhibiting tackiness such as methylcellulose or gum arabic, which are known as sticking agents. Adhesives also include substances known as film-formers, which provide a durable uniform film when applied to a surface. Although an adhesive substance can be included as a constituent of component (d) in the present composition, such inclusion is often not advantageous, because the acrylate/methacrylate-based diblock copolymers of component (b) have adhesive properties. However, including additional adhesive substance is most likely to be advantageous when component (b) is a liquid or paste (i.e., not solid), and particularly when component (b) is a liquid.

The adhesive agent can comprise an adhesive polymer that is natural or synthetic and is without phytotoxic effect on the seed or propagule to be coated. The adhesive agent can be selected from the group consisting of polyvinyl acetates, polyvinyl acetate copolymers, hydrolyzed polyvinyl acetates, polyvinylpyrrolidone-vinyl acetate copolymers, polyvinyl alcohols, polyvinyl alcohol copolymers, polyvinyl methyl ether, polyvinyl methyl ether-maleic anhydride copolymers, waxes, latex polymers, celluloses including ethylcelluloses and methylcelluloses, hydroxymethylcelluloses, hydroxypropylcelluloses, hydroxymethylpropyl-celluloses, polyvinylpyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean protein-based polymers and copolymers, lignosulfonates, acrylic copolymers, starches, polyvinylacrylates, zeins, gelatin, carboxymethylcellulose, chitosan, polyethylene oxide, acrylimide polymers and copolymers, polyhydroxyethyl acrylate, methylacrylimide polymers, alginate, ethylcellulose, polychloroprene, and syrups or mixtures thereof. The above-identified polymers include those known in the art, such as AGRIMER VA 6 and LICOWAX KST. Of note as adhesives are polyvinylpyrrolidinone-vinyl acetate copolymers and water-soluble waxes (e.g., polyethylene glycol).

The total amount of adhesive (i.e., the sum of component (b) and adhesives in component (d)) in the composition adhering to a coated propagule is generally in the range of about 0.001 to 100% of the weight of the propagule. For large seeds, the total amount of adhesive is typically in the range of about 0.05 to 5% of the seed weight; for small seeds the total amount is typically in the range of about 1 to 100%, but can be greater than 100% of seed weight in pelleting. For other propagules, the total amount of adhesive is typically in the range of 0.001 to 2% of the propagule weight.

Optionally, the present composition can contain up to about 10% (based on the weight of the composition) of liquid diluents as a constituent of component (d). In the context of the present disclosure and claims, the term "liquid diluent" excludes water unless otherwise indicated. When the present composition comprises one or more liquid diluents, they generally amount to at least 0.1% of the composition by weight. Typically, as a constituent in a composition coating a propagule, the liquid diluents are relatively nonvolatile, i.e., have a normal boiling point of greater than about 160° C., preferably greater than about 200° C. Examples of liquid diluents include N-alkylpyrrolidones, dimethyl sulfoxide, ethylene glycol, polypropylene glycol, propylene carbonate, dibasic esters, paraffins, alkylnaphthalenes, oils of olive, castor, linseed, tung, sesame, corn, peanut, cottonseed, soybean, rapeseed and coconut, fatty acid esters, ketones such as isophorone and 4-hydroxy-4-methyl-2-pentanone, and alcohols such as cyclohexanol, decanol, benzyl and tetrahydrofurfuryl alcohol. Typical liquid diluents are described in Marsden, Solvents Guide, 2nd Ed., Interscience, New York, 1950. As the presence of liquid diluents can soften a composition coating a propagule, the present composition typically comprises not more than about 5% of liquid diluents by weight.

Optionally, the present composition can contain up to about 75% (based on the weight of the composition) of solid diluents as a constituent of component (d). When the present composition comprises one or more solid diluents, they generally amount to at least 0.1% of the composition by weight. In the context of the present disclosure and claims, solid diluents are considered to be solid substances principally providing bulk instead of other useful (e.g., adhesive, surfactant) properties. Typical solid diluents are described in Watkins et al., *Handbook of Insecticide Dust Diluents and Carriers,* 2nd Ed., Dorland Books, Caldwell, N.J. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. High concentrations of solid diluents (i.e., up to about 75%) are typically included in a composition of the present invention for pelleting seeds. For pelleting seeds, the solid diluents are preferably insoluble, for example, bentonite, montmorillonite, attapulgite and kaolin (clays), silica (e.g., powdered silica) and calcium carbonate (e.g., ground limestone). When the present composition is not intended for pelleting seeds, the amount of solid diluents is typically not more than about 10% of the composition by weight.

The acrylate/methacrylate-based diblock copolymers of component (b) typically obviate the need to include additional surfactants such as wetting agents and dispersants, but one or more such surfactants can be included in the composition as a constituent of component (d). If the present composition includes additional wetting agents or dispersants, they typically are present in an amount of at least about 0.1% of the composition by weight. Typically, the present composition does not include more than about 15%, more typically not more than about 10%, and most typically not more than about 5% of additional surfactants by weight.

Examples of dispersing agents include anionic surfactants such as phosphate esters of tristyrylphenol ethoxylates (e.g., SOPROPHOR 3D33), alkylarylsulfonic acids and their salts (e.g., SUPRAGIL MNS90), lignin sulfonates (e.g., ammonium lignosulfonate or sodium lignosulfonate), polyphenol sulfonates, polyacrylic acids, acrylic graft copolymers such as acrylic acid/methyl methacrylate/polyoxyethylene graft copolymers (e.g., ATLOX 4913), and other polymers combining polyoxyalkylene with acid functionality such as ATLOX 4912 (a block copolymer of polyoxyethylene and hydroxystearic acid).

Examples of wetting agents (some of which overlap with dispersing agents) include alkyl sulfate salts (e.g., SIPON LC 98, sodium lauryl sulfate), alkyl ether sulfate salts (e.g., sodium lauryl ether sulfate), alkylarylsulfonates (i.e., salts of alkylarylsulfonic acids, including arylsulfonic acids substituted with more than one alkyl moiety) such as sodium or calcium alkylbenzenesulfonates (e.g., RHODACAL DS1) and alkylnaphthalenesulfonates (e.g., RHODACAL BX-78), α-olefin sulfonate salts, dialkyl sulfosuccinate salts and salts of polycarboxylic acids.

Additional surfactants include, for example, ethoxylated alcohols, ethoxylated alkylphenols, ethoxylated sorbitan fatty acid esters, ethoxylated sorbitol fatty acid esters, ethoxylated amines, ethoxylated fatty acids and esters (including ethoxylated vegetable oils), organosilicones, N,N-dialkyltaurates, glycol esters, formaldehyde condensates, and block polymers other than acrylate/methacrylate-based diblock copolymers.

Component (d) can also comprise one or more anti-foaming agents. Anti-foaming agents are surfactants that can effectively either prevent foam formation or reduce or eliminate it once it has formed. Examples of anti-foaming agents include silicone oils, mineral oils, polydialkylsiloxanes such as polydimethylsiloxanes, fatty acids and their salts with polyvalent cations such as calcium, magnesium and aluminum, alkyne diols (e.g., SURFYNOL 104), and fluoroaliphatic esters, perfluoroalkylphosphonic and perfluoroalkylphosphinic acids, and salts thereof. When the present composition comprises one or more anti-foaming agents, they typically amount to at least about 0.01% and not more than about 3% of the composition by weight. More typically, anti-foaming agents are not more than about 2% and most typically not more than about 1% of the composition by weight.

*McCutcheon's Emulsifiers and Detergents and McCutcheon's Functional Materials* (North America and International Editions, 2001), The Manufacturing Confection Publ. Co., Glen Rock, N.J., as well as Sisely and Wood, Encyclopedia of Surface Active Agents, Chemical Publ. Co., Inc., New York, 1964, list surfactants and recommended uses.

Component (d) can comprise one or more antifreeze agents. Antifreeze agents prevent freezing of the composition of the present invention extended with an aqueous liquid carrier before coating on propagules. Examples of antifreeze agents include glycols such as ethylene glycol, diethylene glycol, propylene glycol, dipropylene glycol, glycerol, 1,3-propanediol, 1,2-propanediol and polyethylene glycol of molecular weight in the range from about 200 to about 1,000 daltons. Antifreeze agents of note for the composition of the present invention include ethylene glycol, propylene glycol, glycerol, 1,3-propanediol and 1,2-propanediol. When component (d) comprises one or more antifreeze agents, they typically amount to at least about 0.1% and not more than about 14% of the composition by weight. More typically, antifreeze agents do not amount to more than 10% and most typically not more than about 8% of the total weight of the composition.

Component (d) can comprise one or more thickening agents. Thickening agents (i.e., thickeners) increase the viscosity of the continuous liquid medium formed when the present composition is extended with an aqueous liquid carrier. By increasing viscosity, the propensity of solid particles (e.g., of component (a)) to settle is reduced. Because component (b) also increases viscosity, including one or more thickening agents in component (d) is generally not necessary and indeed can be unhelpful if the viscosity of the composition is already as much as desired. Including one or more thickening agents in component (d) can be beneficial for slowing settling of particles of component (a) if the composition is extended with a large amount of aqueous liquid carrier relative to component (b), particularly when component (b) comprises mainly acrylate/methacrylate-based diblock copolymers of relatively low molecular weight (i.e., less than about 5,000 daltons). Examples of thickening agents useful for the present composition include polyols such as glycerol, polysaccharides including heteropolysaccharides such as xanthan gum, and hydrated clays with very small particle sizes (e.g., 2 nm) such as the hydrated magnesium aluminosilicate ACTI-GEL 208 (Active Minerals). Glycerol is of note as having both antifreeze and thickener properties. An extensive list of thickeners and their applications can be found in *McCutcheon's* 2005*, Volume* 2*: Functional Materials* published by MC Publishing Company. If component (d) comprises one or more thickening agents, they typically amount to at least about 0.1% and not greater than about 5% of the composition by weight.

Component (d) can comprise a preservative constituent consisting essentially of one or more stabilizing agents or biocides, and the amount of the preservative constituent is typically up to about 1% of the composition by weight. When a preservative constituent is present, it typically amounts to at least about 0.01% of the composition by weight. The preservative constituent does not exceed typically about 1%, more typically about 0.5% and most typically about 0.3% of the total weight of the composition.

Stabilizing agents, for example, anti-oxidants (such as butylhydroxytoluene) or pH modifiers (such as citric acid or acetic acid) can prevent decomposition of active ingredients (i.e., component (a) and/or component (c)) during storage. Biocides can prevent or reduce microbial contamination within a formulated composition. Particularly suitable biocides are bactericides such as LEGEND MK (a mixture of 5-chloro-2-methyl-3(2H)-isothiazolone with 2-methyl-3(2H)-isothiazolone), EDTA (ethylenediaminetetraacetic acid), formaldehyde, benzoic acid, and 1,2-benzisothiazol-3(2H)-one or its salts (e.g., PROXEL BD or PROXEL GXL (Arch Chemicals, Inc.)). Of note is the present composition wherein component (d) comprises a biocide, in particular, a bactericide such as 1,2-benzisothiazol-3(2H)-one or one of its salts.

Component (d) can also comprise one or more fertilizers. Fertilizers included in component (d) can provide plant nutrients such as nitrogen, phosphorus and potassium and/or micronutrients such as manganese, iron, zinc and molybdenum. Of note for inclusion in component (d) are micronutrients such as manganese, iron, zinc and molybdenum. If one or more fertilizers are present, they typically amount to at least about 0.1% and not more than about 20% of the composition by weight, although greater amounts can be included.

Other formulation ingredients can be included in the present composition as component (d), such as rheology modifiers, dyes, and the like. These ingredients are known to one skilled in the art and can be found described, for example, in *McCutcheon's, Volume* 2*: Functional Materials* published by MC Publishing Company annually.

One aspect of the present invention is a geotropic propagule coated with an insecticidally effective amount of the aforedescribed composition. Geotropic propagules include seeds. The present invention is applicable to virtually all seeds, including seeds of wheat (*Triticum aestivum* L.), durum wheat (*Triticum durum* Desf.), barley (*Hordeum vulgare* L.), oat (*Avena sativa* L.), rye (*Secale cereale* L.), maize (*Zea mays* L.), sorghum (*Sorghum vulgare* Pers.), rice (*Oryza sativa* L.), wild rice (*Zizania aquatica* L.), cotton (*Gossypium barbadense* L. and *G. hirsutum* L.), flax (*Linum usitatissimum* L.), sunflower (*Helianthus annuus* L.), soybean (*Glycine max* Merr.), garden bean (*Phaseolus vulgaris* L.), lima bean (*Phaseolus limensis* Macf.), broad bean (*Vicia faba* L.), garden pea (*Pisum sativum* L.), peanut (*Arachis hypogaea* L.), alfalfa (*Medicago sativa* L.), beet (*Beta vulgaris* L.), garden lettuce (*Lactuca sativa* L.), rapeseed (*Brassica rapa* L. and *B. napus* L.), cole crops such as cabbage, cauliflower and broccoli (*Brassica oleracea* L.), turnip (*Brassica rapa* L.), leaf (oriental) mustard (*Brassica juncea* Coss.), black mustard (*Brassica nigra* Koch), tomato (*Lycopersicon esculentum* Mill.), potato (*Solanum tuberosum* L.), pepper (*Capsicum frutescens* L.), eggplant (*Solanum melongena* L.), tobacco (*Nicotiana tabacum*), cucumber (*Cucumis sativus* L.), muskmelon (*Cucumis melo* L.), watermelon (*Citrullus vulgaris* Schrad.), squash (*Curcurbita pepo* L., *C. moschata* Duchesne. and *C. maxima* Duchesne.), carrot (*Daucus carota* L.), zinnia (*Zinnia elegans* Jacq.), cosmos (e.g., *Cosmos bipinnatus* Cay.), chrysanthemum (*Chrysanthemum* spp.), sweet scabious (*Scabiosa atropurpurea* L.), snapdragon (*Antirrhinum majus* L.), gerbera (*Gerbera jamesonii* Bolus), babys-breath (*Gypsophila paniculata* L., *G. repens* L. and *G. elegans* Bieb.), statice (e.g., *Limonium sinuatum* Mill., *L. sinense* Kuntze.), blazing star (e.g., *Liatris spicata* Willd., *L. pycnostachya* Michx., *L. scariosa* Willd.), lisianthus (e.g., *Eustoma grandiflorum* (Raf.) Shinn), yarrow (e.g., *Achillea filipendulina* Lam., *A. millefolium* L.), marigold (e.g., *Tagetes patula* L., *T. erecta* L.), pansy (e.g., *Viola cornuta* L., *V. tricolor* L.), impatiens (e.g., *Impatiens balsamina* L.), petunia (*Petunia* spp.), geranium (*Geranium* spp.) and coleus (e.g., *Solenostemon scutellarioides* (L.) Codd). Geotropic propagules also include rhizomes, tubers, bulbs or corms, or viable divisions thereof. Suitable rhizomes, tubers, bulbs and corms, or viable divisions thereof include those of potato (*Solanum tuberosum* L.), sweet potato (*Ipomoea batatas* L.), yam (*Dioscorea cayenensis* Lam. and *D. rotundata* Poir.), garden onion (e.g., *Allium cepa* L.), tulip (*Tulipa* spp.), gladiolus (*Gladiolus* spp.), lily (*Lilium* spp.), narcissus (*Narcissus* spp.), dahlia (e.g., *Dahlia pinnata* Cay.), iris (*Iris germanica* L. and other species), crocus (*Crocus* spp.), anemone (*Anemone* spp.), hyacinth (*Hyacinth* spp.), grape-hyacinth (*Muscari* spp.), freesia (e.g., *Freesia refracta* Klatt., *F. armstrongii* W. Wats), ornamental onion (*Allium* spp.), wood-sorrel (*Oxalis* spp.), squill (*Scilla peruviana* L. and other species), cyclamen (*Cyclamen persicum* Mill. and other species), glory-of-the-snow (*Chionodoxa luciliae* Boiss. and other species), striped squill (*Puschkinia scilloides* Adams), calla lily (*Zantedeschia aethiopica* Spreng., *Z. elliottiana* Engler and other species), gloxinia (*Sinnigia speciosa* Benth. & Hook.) and tuberous begonia (*Begonia tuberhybrida* Voss.). The above recited cereal, vegetable, ornamental (including flower) and fruit crops are illustrative, and should not be considered limiting in any way. For reasons of insect control spectrum and economic importance, embodiments coating seeds of cotton, maize, soybean, rapeseed and rice, and coating tubers and bulbs of potato, sweet potato, garden onion, tulip, daffodil, crocus and hyacinth are of note. Also of note are embodiments wherein the geotropic propagule is a seed.

The present composition can be coated on geotropic propagules that contain genetic material introduced by genetic engineering (i.e., transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD, KNOCKOUT, STARLINK, BOLLGARD, NuCOTN and NEWLEAF, and herbicide-tolerant varieties of corn, cotton, soybean and rapeseed such as ROUNDUP READY, LIBERTY LINK, IMI, STS and CLEARFIELD, as well as crops expressing N-acetyltransferase (GAT) to provide resistance to glyphosate herbicide, or crops containing the HRA gene providing resistance to herbicides inhibiting acetolactate synthase (ALS). The present insecticidal composition may interact synergistically with traits introduced by genetic engineering or modified by mutagenesis, thus enhancing phenotypic expression or effectiveness of the traits or increasing the insect control effectiveness of the present composition. In particular, the present insecticidal composition may interact synergistically with the phenotypic expression of proteins or other natural products toxic to invertebrate pests to provide greater-than-additive control of these pests.

The thickness of coatings of the present composition on geotropic propagules can vary from thin films 0.001 mm thick to layers about 0.5 to 5 mm thick. Generally, a coating that increases the weight of a seed up to 25% is defined as a film coating. Film-coated seed retains the shape and the general size of the uncoated seed. A coating that increases the weight of the seed more than 25% is referred to as a pellet coating. Coatings on geotropic propagules can comprise more than one adhering layer, only one of which need comprise the present composition. Generally pellets are more satisfactory for small seeds, because their ability to provide an insecticidally effective amount of the present composition is not limited by the surface area of the seed, and pelleting small seeds also facilitates seed transfer and planting operations. Because of their larger size and surface area, large seeds and bulbs, tubers, corms and rhizomes and their viable cuttings are generally not pelleted, but instead coated with a thin film.

For application of a coating of the aforedescribed composition to a geotropic propagule, the composition is typically first extended with a volatile aqueous liquid carrier to provide a liquid composition consisting of about 5 to 80 weight % of the aforedescribed (unextended) composition (i.e., mixture comprising components (a), (b) and optionally (c) and (d)) and about 20 to 95 weight % of the volatile aqueous liquid carrier. Alternatively and more typically, one or more of the composition components is first mixed with the volatile aqueous liquid carrier before the components are combined to provide the liquid composition containing components (a), (b) and optionally (c) and (d) in combination with about 20-95 weight % of the volatile aqueous liquid carrier. The amount of volatile liquid carrier is more typically at least about 25% and most typically at least about 30% of the liquid composition by weight. Also, the amount of volatile liquid carrier is more typically not more than about 70% of the liquid composition by weight.

In the context of the present disclosure and claims, the expression "volatile aqueous liquid carrier" refers to a composition consisting of at least about 50% water by weight and optionally one or more water-soluble compounds that are liquid at 20° C. and have a normal boiling point of not greater than about 100° C. These water-soluble liquid compounds should be nonphytotoxic to the geotropic propagule to be coated. Examples of such water-soluble liquid compounds are acetone, methyl acetate, methanol and ethanol. However, a volatile aqueous liquid carrier mostly or entirely of water is typically preferable, because water is inexpensive, nonflammable, environmentally friendly and nonphytotoxic. Typically, the volatile aqueous liquid carrier comprises at least about 80%, more typically at least about 90%, and most typically at least about 95% water by weight. In some embodiments, the volatile aqueous liquid carrier consists essentially of water. In some embodiments, the volatile liquid carrier is water.

In the liquid composition comprising the volatile aqueous liquid carrier, the volatile aqueous liquid carrier forms a continuous liquid phase in which other components (e.g., components (a), (b) and optionally (c) and (d)) are suspended or dissolved. Typically, at least some of component (a) is present as particles suspended in the continuous liquid phase and therefore the liquid composition can be described as a suspension concentrate composition. In some embodiments at least about 90%, or 95% or 98% of component (a) is present as particles suspended in the continuous liquid phase. Typically, more than 95% by weight of the particles have a particle size less than about 10 microns.

The aggregation state of the acrylate/methacrylate-based diblock copolymers component (i.e., component (b)) in the liquid composition depends on such parameters as ingredients, concentration, temperature and ionic strength. The liquid composition typically comprises suspended particles of component (a) having large surface areas. Acrylate/methacrylate-based diblock copolymer molecules are generally adsorbed to such interfaces (e.g., as monolayers, bilayers or hemimicelles) in preference to remaining in solution, and only when the interfaces are saturated do high concentrations of the molecules remain in the aqueous phase. Therefore the presence of particles of component (a) allows the liquid composition to accommodate more of component (b) without forming a separate component (b) phase than would be expected based solely on water solubility. If the liquid composition contains component (b) in excess of both its adsorption onto component (a) particles and its solubility in the aqueous carrier phase, a portion of component (b) will be present in a discrete phase, either as solid particles or as liquid droplets depending upon the physical properties (e.g., melting point) of component (b).

The liquid composition comprising the volatile aqueous liquid carrier is often most conveniently prepared by mixing components (a) and (b) and optionally (c) and (d) with the volatile aqueous liquid carrier (e.g., water). As noted above, component (b) is water-soluble to the extent of at least 5% at 20° C. For ease of dissolution of component (b) in the formulation, it is preferred to dissolve component (b) in the aqueous liquid carrier prior to mixing with the other ingredients.

In the liquid composition, the median particle size of particles of component (a) is preferably less than about 10 microns to provide good suspensibility as well as high biological availability and coating coverage of the propagule. More preferably the median particle size of component (a) is less than 4 microns or 3 microns or 2 microns and most preferably less than about 1 micron. Typically, the median particle size is at least about 0.1 micron, but smaller particle sizes are suitable.

Milling can be used to reduce the particle size of component (a) as well as other solid components. Milling methods are well-known and include ball-milling, bead-milling, sand-milling, colloid-milling and air-milling. These can be combined with high-speed blending, which typically involves high shear, to prepare suspensions and dispersions of particles. Of particular note is ball- or bead-milling for reducing the particle size of component (a). Other components, such as component (b), can be included in the mixture for milling or later mixed with the milled mixture. However, other components comprising solid particles initially having a particle size of greater than 10 microns and low water solubility are typically included in the mixture for milling. Although acrylate/methacrylate-based diblock copolymer component (b) and optional additional surfactant of component (d) can be added after milling component (a), typically a portion of component (b) and/or optional additional surfactant is included in the mixture to facilitate milling component (a) to small particle size.

Milling is often unneeded in methods for preparing the liquid composition by first dissolving component (a) in an organic solvent. In one method, components (a) and (b) and optionally other components are dissolved in an organic solvent, and then a miscible solvent in which components (a) and (b) are much less soluble is added to the solution of components (a) and (b) to form a precipitate. The precipitate is collected and suspended in the volatile aqueous liquid carrier (e.g., water) for coating propagules. N-methyl-2-pyrrolidone and diethyl ether are suitable as the more soluble and less soluble solvents, respectively, when the acrylate/methacrylate-based diblock copolymers of component (b) have a high polyoxyethylene content (e.g., about 80% or greater), thus causing low solubility in diethyl ether.

In a related method, components (a) and (b) and optionally other components are dissolved in an organic solvent system comprising a lower boiling solvent in which component (a) is very soluble and a higher boiling solvent in which component (a) is less soluble (e.g., a binary solvent system of dichloromethane and ethanol), and then the solvent is evaporated under vacuum. The residue is then suspended in the volatile aqueous liquid carrier (e.g., water) for coating propagules.

In another method, component (a) and component (b) are dissolved in a water-miscible organic solvent such as N-methyl-2-pyrrolidone. The solution is then placed inside a sealed dialysis membrane, which is selected to allow the organic solvent and water to equilibrate but not allow passage of component (b). The sealed dialysis membrane is then placed in water to allow replacement of the organic solvent with water. Water entering the dialysis membrane causes component (a) to crystallize and form a slurry. The resultant aqueous slurry is used to coat propagules.

After the liquid composition comprising the volatile aqueous liquid carrier has been prepared, it can be applied to the surface of a propagule by any of several techniques known in the art, which involve evaporating the volatile aqueous liquid carrier to leave a coating of the insecticidal composition comprising components (a), (b) and optionally (c) and (d) adhering to the surface of the propagule. Various coating machines and processes are available to one skilled in the art. Suitable processes include those listed in P. Kosters et al., Seed Treatment: Progress and Prospects, 1994 BCPC Monograph No. 57 and the references listed therein. Coating processes are also described in U.S. Pat. Nos. 5,527,760 and 6,202,345. Three well-known techniques include the use of drum coaters, fluidized bed techniques and spouted beds. Seeds can be presized prior to coating. After coating, the seeds are dried and then optionally sized by transfer to a sizing machine. These machines are known in the art.

In one method, propagules are coated by spraying the liquid composition comprising the volatile aqueous liquid carrier directly into a tumbling bed of seeds and then drying the propagules. In one embodiment for coating seeds, the seed and coating material are mixed in a conventional seed coating apparatus. The rate of rolling and application of coating depends upon the seed. For large oblong seeds such as that of cotton, a satisfactory seed coating apparatus comprises a rotating type pan with lifting vanes turned at sufficient rpm to maintain a rolling action of the seed, facilitating uniform coverage. The seed coating must be applied over sufficient time to allow drying to minimize clumping of the seed. Using forced air or heated forced air can allow increasing the rate of application. One skilled in the art will also recognize that this process may be a batch or continuous process. As the name implies, a continuous process allows the seeds to flow continuously throughout the product run. New seeds enter the pan in a steady stream to replace coated seeds exiting the pan.

One embodiment of seed coating is seed pelleting. The pelleting process typically increases the seed weight from 2 to 100 times and can be used to also improve the shape of the seed for use in mechanical seeders. Pelleting compositions generally contain a solid diluent, which is typically an insoluble particulate material, such as clay, ground limestone, or powdered silica to provide bulk in addition to a film-former or sticking agent. Depending on the extent of coating applied, pelletizing may provide a spherical shape to the seeds which are normally elongated or irregularly shaped. A method for producing pellets is described in Agrow, *The Seed Treatment Market*, Chapter 3, PJB Publications Ltd., 1994.

One aspect of the present invention is a method for protecting a geotropic propagule and plant derived therefrom from a phytophagous insect pest by coating the propagule with an insecticidally effective amount of the liquid composition comprising components (a), (b) and optionally (c) and (d) along with a volatile aqueous liquid carrier and then evaporating the volatile aqueous liquid carrier of the composition. This coating process constitutes a treatment of the propagule by providing a coating of an insecticidally effective amount of the insecticidal composition on the propagule. The coating of the composition on the propagule provides an insecticidally effective amount of component (a) (i.e., one or more anthranilic diamide insecticides) available for absorption into the propagule and/or roots developing from the propagule. In some embodiments, the acrylate/methacrylate-based diblock copolymer of component (b) have been discovered to increase the absorption of component (a) into the propagules and/or developing roots to provide through xylem transport an insecticidally effective concentration of component (a) in even foliage developing from the coated propagule. Sufficiently increasing the absorption can raise concentrations of component (a) above the minimum concentration for insecticidal effectiveness in not only the lower foliage but also middle to upper foliage, and provide protection later into the growing season. Insecticidally effective concentrations of component (a) protect the propagule and derived plant from injury or damage caused by a phytophagous insect pest by controlling the insect pest. This control can include killing the insect pest, interfering with its growth, development or reproduction, and/or inhibiting its feeding. Typically, control involves feeding inhibition and death of the insect pest.

Generally to protect a seed and foliage developing therefrom from a phytophagous insect pest, the present composition is coated on a geotropic propagule to provide component (a) in an amount ranging from about 0.001 to 50% of the weight of the propagule, for seeds more often in the range of about 0.01 to 50% of the seed weight, and most typically for large seeds in the range of about 0.01 to 10% of the seed weight. However, larger amounts up to about 100% or more are useful, particularly for pelleting small seed for extended invertebrate pest control protection. For propagules such as bulbs, tubers, corms and rhizomes and their viable cuttings, generally the amount of component (a) included in the composition coating ranges from about 0.001 to 5% of the propagule weight, with the higher percentages used for smaller propagules. One skilled in the art can easily determine the insecticidally effective amount of the present composition and component (a) necessary for the desired level of phytophagous insect pest control and seed and plant protection.

As referred to in this disclosure, the term "phytophagous insect pest" includes larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hubner), black cutworm (*Agrotis ipsilon* Hufnagel), cabbage looper (*Trichoplusia ni* Hubner), and tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hubner), navel orangeworm (*Amyelois transitella* Walker), corn root webworm (*Crambus caliginosellus* Clemens), and sod webworm (*Herpetogramma licarsisalis* Walker)); leafrollers, budworms, seed worms, and fruit worms in the family Tortricidae (e.g., codling moth (*Cydia pomonella* L. (L. means *Linnaeus*)), grape berry moth (*Endopiza viteana* Clemens), and oriental fruit moth (*Grapholita molesta* Busck)); and many other economically important lepidoptera (e.g., diamondback moth (*Plutella xylostella* L. of family Plutellidae), pink bollworm (*Pectinophora gossypiella* Saunders of family Gelechiidae), and gypsy moth (*Lymantria dispar* L. of family Lymantriidae)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), and rice weevil (*Sitophilus oryzae* L.)); flea beetles, cucumber beetles, rootworms, leaf beetles, potato beetles, and leafminers in the family *Chrysomelidae* (e.g., Colorado potato beetle (*Leptinotarsa decemlineata* Say), and western corn rootworm (*Diabrotica virgifera* virgifera LeConte)); chafers and other beetles from the family Scarabaeidae (e.g., Japanese beetle (*Popillia japonica* Newman) and European chafer (*Rhizotrogus majalis* Razoumowsky)); wireworms from the family Elateridae and bark beetles from the family Scolytidae; adults and larvae of the order Dermaptera including earwigs from the family Forficulidae (e.g., European earwig (*Forficula auricularia* L.) and black earwig (*Chelisoches morio* Fabricius)); adults and nymphs of the orders Hemiptera and Homoptera such as, plant bugs from the family Miridae, cicadas from the family Cicadidae, leafhoppers (e.g., *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae, squash bugs from the family Coreidae, and red bugs and cotton stainers from the family Pyrrhocoridae; adults and immatures of the order Orthoptera including grasshoppers, locusts and crickets (e.g., migratory grasshoppers (e.g., *Melanoplus sanguinipes* Fabricius and *M. differentialis* Thomas), American grasshoppers (e.g., *Schistocerca americana* Drury), desert locust (*Schistocerca gregaria* Forskal), migratory locust (*Locusta migratoria* L.), and mole crickets (*Gryllotalpa* spp.)); adults and immatures of the order Diptera, including leafminers, midges, fruit flies (Tephritidae), frit flies (e.g., *Oscinella frit* L.), soil maggots and other Nematocera; adults and immatures of the order Thysanoptera including onion thrips (*Thrips tabaci* Lindeman) and other foliar feeding thrips. Of note is the present method for protecting a propagule or plant derived therefrom from a phytophagous insect pest wherein the insect pest is in a taxonomic order selected from Hemiptera (particularly the families Aleyrodidae, Aphidadae, Cicadellidae, and Delphacidae) and Lepidoptera (particularly the families Gelechiidae, Lymantriidae, Noctuidae, Plutellidae, Pyralidae and Torticidae). Of particular note is the present method wherein the insect pest is in the family Noctuidae.

Embodiments of the present invention include:

Embodiment 1

The insecticidal composition described in the Summary of the Invention comprising by weight based on the total weight of the composition:

(a) from about 9 to about 91% of one or more anthranilic diamide insecticides; and (b) from about 9 to about 91% of an acrylate/methacrylate (A/MA)-based diblock copolymer component having a water solubility of at least about 5% by weight at 20° C., a hydrophilic-lipophilic balance value of at least about 3, and an average molecular weight ranging from about 1,500 to about 50,000 daltons;

wherein the ratio of component (b) to component (a) is about 1:10 to about 10:1 by weight.

Embodiment 2

The composition of Embodiment 1 wherein component (a) (i.e., one or more anthranilic diamide insecticides) comprises at least one compound selected from anthranilic diamides of Formula 1, N-oxides, and salts thereof,

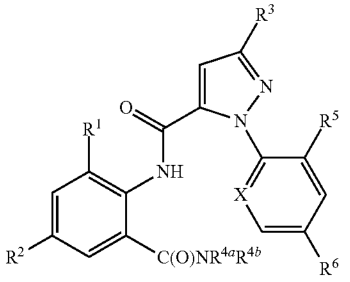

wherein
X is N, CF, CCl, CBr or Cl;
$R^1$ is $CH_3$, Cl, Br or F;
$R^2$ is H, F, Cl, Br or —CN;
$R^3$ is F, Cl, Br, $C_1$-$C_4$ haloalkyl or $C_1$-$C_4$ haloalkoxy;
$R^{4a}$ is H, $C_1$-$C_4$ alkyl, cyclopropylmethyl or 1-cyclopropylethyl;
$R^{4b}$ is H or $CH_3$;
$R^5$ is H, F, Cl or Br; and
$R^6$ is H, F, Cl or Br.

Embodiment 3

The composition of Embodiment 2 wherein component (a) is selected from anthranilic diamides of Formula 1, N-oxides, and salts thereof.

Embodiment 4

The composition of Embodiment 3 wherein component (a) is selected from anthranilic diamides of Formula 1 and salts thereof.

Embodiment 5

The composition of Embodiment 4 wherein component (a) is selected from anthranilic diamides of Formula 1.

Embodiment 6

The composition of any one of Embodiments 2 through 5 wherein X is N; $R^1$ is $CH_3$; $R^2$ is Cl or —CN; $R^3$ is Cl, Br or $CF_3$; $R^{4a}$ is $C_1$-$C_4$ alkyl; Rob is H; $R^5$ is Cl; and $R^6$ is H.

Embodiment 7

The composition of Embodiment 6 wherein $R^{4a}$ is $CH_3$ or $CH(CH_3)_2$.

Embodiment 8

The composition of Embodiment 7 wherein $R^3$ is Br; and $R^{4a}$ is $CH_3$ (i.e., the compound of Formula 1 is chlorantraniliprole or cyantraniliprole, or optionally an N-oxide or salt thereof).

Embodiment 9

The composition of Embodiment 8 wherein $R^2$ is Cl (i.e., the compound of Formula 1 is chlorantraniliprole, or optionally an N-oxide or salt thereof).

Embodiment 10

The composition of Embodiment 8 wherein $R^2$ is —CN (i.e., the compound of Formula 1 is cyantraniliprole, or optionally an N-oxide or salt thereof).

Embodiment 11

The composition of any one of Embodiments 1 through 10 wherein component (a) is at least about 10% of the composition by weight.

Embodiment 12

The composition of Embodiment 11 wherein component (a) is at least about 20% of the composition by weight.

Embodiment 13

The composition of Embodiment 12 wherein component (a) is at least about 30% of the composition by weight.

Embodiment 14

The composition of Embodiment 13 wherein component (a) is at least about 40% of the composition by weight.

Embodiment 15

The composition of any one of Embodiments 1 through 14 wherein component (a) is not more than about 90% of the composition by weight.

Embodiment 16

The composition of Embodiment 15 wherein component (a) is not more than about 80% of the composition by weight.

Embodiment 17

The composition of Embodiment 16 wherein component (a) is not more than about 70% of the composition by weight.

Embodiment 18

The composition of any one of Embodiments 1 through 17 wherein not more than about 30% of component (a) is present in the composition as solid particles having a particle size greater than about 10 microns.

Embodiment 19

The composition of Embodiment 18 wherein not more than about 20% of component (a) is present in the composition as solid particles having a particle size greater than about 10 microns.

Embodiment 20

The composition of Embodiment 20 wherein not more than about 10% of component (a) is present in the composition as solid particles having a particle size greater than about 10 microns.

Embodiment 21

The composition of any one of Embodiments 1 through 20 wherein component (b) (i.e., the acrylate/methacrylate-based diblock copolymer component) has a water solubility of at least about 10% at 20° C.

Embodiment 22

The composition of Embodiment 21 wherein component (b) has a water solubility of at least about 25% at 20° C.

Embodiment 23

The composition of any one of Embodiments 1 through 22 wherein component (b) has a hydrophilic-lipophilic balance (HLB) value of at least about 6.

Embodiment 24

The composition of Embodiment 23 wherein component (b) has an HLB value of at least about 7.

Embodiment 25

The composition of Embodiment 24 wherein component (b) has an HLB value of at least about 8.

Embodiment 26

The composition of Embodiment 25 wherein component (b) has an HLB value of at least about 10.

Embodiment 27

The composition of Embodiment 26 wherein component (b) has an HLB value of at least about 20.

Embodiment 28

The composition of Embodiment 27 wherein component (b) has an HLB value of at least about 22.

Embodiment 29

The composition of any one of Embodiments 1 through 28 wherein component (b) has an HLB value of not more than about 40.

Embodiment 30

The composition of Embodiment 29 wherein component (b) has an HLB value of not more than about 35.

Embodiment 31

The composition of Embodiment 30 wherein component (b) has an HLB value of not more than about 31.

Embodiment 32

The composition of any one of Embodiments 1 through 27 wherein component (b) has an HLB value of not more than about 20.

Embodiment 33

The composition of any one of Embodiments 1 through 26 wherein component (b) has an HLB value of not more than about 15.

Embodiment 34

The composition of any one of Embodiments 1 through 33 wherein component (b) (separate from the composition) is a paste or solid at 20° C.

Embodiment 35

The composition of any one of Embodiments 1 through 32 wherein component (b) (separate from the composition) is a solid at 20° C.

Embodiment 36

The composition of any one of Embodiments 1 through 35 wherein component (b) has an average molecular weight of at least about 5,000 daltons.

Embodiment 37

The composition of Embodiment 36 wherein component (b) has an average molecular weight of at least about 15,000 daltons.

Embodiment 38

The composition of Embodiment 37 wherein component (b) has an average molecular weight of at least about 25,000 daltons.

Embodiment 39

The composition of Embodiment 38 wherein component (b) has an average molecular weight of at least about 35,000 daltons.

Embodiment 40

The composition of any one of Embodiments 1 through 36 wherein component (b) has an average molecular weight of not more than about 10,000 daltons.

Embodiment 41

The composition of Embodiment 37 wherein component (b) has an average molecular weight of not more than about 7,000 daltons.

Embodiment 42

The composition of any one of Embodiments 1 through 41 wherein component (b) (i.e., the acrylate/methacrylate-based diblock copolymer component) is at least about 10% of the composition by weight.

Embodiment 43

The composition of Embodiment 42 wherein component (b) is at least about 15% of the composition by weight.

Embodiment 44

The composition of Embodiment 43 wherein component (b) is at least about 20% of the composition by weight.

Embodiment 45

The composition of Embodiment 44 wherein component (b) is at least about 25% of the composition by weight.

Embodiment 46

The composition of Embodiment 45 wherein component (b) is at least about 30% of the composition by weight.

Embodiment 47

The composition of Embodiment 46 wherein component (b) is at least about 35% of the composition by weight.

Embodiment 48

The composition of Embodiment 47 wherein component (b) is at least about 40% of the composition by weight.

Embodiment 49

The composition of any one of Embodiments 1 through 48 wherein component (b) is not more than about 80% of the composition by weight.

Embodiment 50

The composition of Embodiment 49 wherein component (b) is not more than about 70% of the composition by weight.

Embodiment 51

The composition of Embodiment 50 wherein component (b) is not more than about 60% of the composition by weight.

Embodiment 52

The composition of Embodiment 51 wherein component (b) is not more than about 50% of the composition by weight.

Embodiment 53

The composition of Embodiment 52 wherein component (b) is not more than about 40% of the composition by weight.

Embodiment 54

The composition of any one of Embodiments 1 through 53 wherein the ratio of component (b) to component (a) is at least about 1:8 (by weight).

Embodiment 55

The composition of Embodiment 54 wherein the ratio of component (b) to component (a) is at least about 1:5.

Embodiment 56

The composition of Embodiment 55 wherein the ratio of component (b) to component (a) is at least about 1:4.

Embodiment 57

The composition of Embodiment 56 wherein the ratio of component (b) to component (a) is at least about 1:3.

Embodiment 58

The composition of Embodiment 57 wherein the ratio of component (b) to component (a) is at least about 1:2.

Embodiment 59

The composition of Embodiment 58 wherein the ratio of component (b) to component (a) is at least about 1:1.

Embodiment 60

The composition of Embodiment 59 wherein the ratio of component (b) to component (a) is at least about 2:1.

Embodiment 61

The composition of Embodiment 60 wherein the ratio of component (b) to component (a) is at least about 3:1.

Embodiment 62

The composition of Embodiment 61 wherein the ratio of component (b) to component (a) is at least about 4:1.

Embodiment 63

The composition of Embodiment 62 wherein the ratio of component (b) to component (a) is at least about 8:1.

Embodiment 64

The composition of any one of Embodiments 1 through 59 wherein the ratio of component (b) to component (a) is not more than about 1:1.

Embodiment 65

The composition described in the Summary of the Invention or any one of Embodiments 1 through 64 wherein component (b) comprises one or more acrylate/methacrylate-based diblock copolymers.

Embodiment 66

The composition of Embodiment 65 wherein component (b) comprises one or more acrylate/methacrylate-based diblock copolymers.

Embodiment 67

The composition of Embodiment 65 or 66 wherein component (b) comprises one or more acrylate/methacrylate-based diblock copolymers.

Embodiment 68

The composition of Embodiment 67 wherein component (b) consists essentially of one or more acrylate/methacrylate-based diblock copolymers.

Embodiment 69

The composition of Embodiment 67 or 68 wherein the acrylate/methacrylate-based diblock copolymers have a hydrophobic acrylate/methacrylate chain with an average molecular weight of at least about 900 daltons.

Embodiment 70

The composition of Embodiment 69 wherein the hydrophobic acrylate/methacrylate chain has an average molecular weight of at least about 1,200 daltons.

Embodiment 71

The composition of Embodiment 70 wherein the hydrophobic acrylate/methacrylate chain has an average molecular weight of at least about 1,700 daltons.

Embodiment 72

The composition of Embodiment 71 wherein the hydrophobic acrylate/methacrylate chain has an average molecular weight of at least about 2,000 daltons.

Embodiment 73

The composition of any one of Embodiments 67 through 72 wherein the acrylate/methacrylate-based diblock copolymers have a hydrophobic acrylate/methacrylate chain with an average molecular weight of not more than about 5,000 daltons.

Embodiment 74

The composition of Embodiment 73 wherein the hydrophobic acrylate/methacrylate chain has an average molecular weight of not more than about 4,000 daltons.

Embodiment 75

The composition of Embodiment 74 wherein the hydrophobic acrylate/methacrylate chain has an average molecular weight of not more than about 3,000 daltons.

Embodiment 76

The composition of any one of Embodiments 64 through 75 wherein the acrylate/methacrylate-based diblock copolymers have a hydrophilic content of at least about 5% by weight.

Embodiment 77

The composition of Embodiment 76 wherein the hydrophilic content is at least about 15% by weight.

Embodiment 78

The composition of Embodiment 77 wherein the hydrophilic content is at least about 20% by weight.

Embodiment 79

The composition of Embodiment 78 wherein the hydrophilic content is at least about 25% by weight.

Embodiment 80

The composition of Embodiment 79 wherein the hydrophilic content is at least about 35% by weight.

Embodiment 81

The composition of Embodiment 80 wherein the hydrophilic content is at least about 45% by weight.

Embodiment 82

The composition of Embodiment 81 wherein the hydrophilic content is at least about 55% by weight.

Embodiment 83

The composition of Embodiment 82 wherein the hydrophilic content is at least about 65% by weight.

Embodiment 84

The composition of Embodiment 83 wherein the hydrophilic content is at least about 75% by weight.

Embodiment 85

The composition of any one of Embodiments 64 through 84 wherein the acrylate/methacrylate-based diblock copolymers have a hydrophilic content of not more than about 99% by weight.

Embodiment 86

The composition of Embodiment 85 wherein the hydrophilic content is not more than about 10% by weight.

Embodiment 87

The composition of Embodiment 86 wherein component (c) comprises one or more biologically active agents other than anthranilic diamide insecticides and is at least 0.1% of the composition by weight.

Embodiment 88

The composition of Embodiment 87 wherein component (c) is at least 1% of the composition by weight.

Embodiment 89

The composition of any one of Embodiments 86 through 88 wherein component (c) is not more than about 60% of the composition by weight.

Embodiment 90

The composition of Embodiment 89 wherein component (c) is not more than about 20% of the composition by weight.

Embodiment 91

The composition of any one of Embodiments 86 through 90 wherein component (c) comprises at least one fungicide or insecticide (other than anthranilic diamide insecticides).

Embodiment 92

The composition of Embodiment 91 wherein component (c) comprises at least one insecticide.

Embodiment 93

The composition of Embodiment 91 or 92 wherein component (c) comprises at least one fungicide.

Embodiment 94

The composition of any one of Embodiments 1 through 90 wherein the composition does not comprise a biologically active agent other than component (a).

Embodiment 95

The composition of any one of Embodiments 1 through 94 wherein the composition further comprises (d) up to about 80% by weight of one or more inert formulating ingredients other than acrylate/methacrylate-based diblock copolymers.

Embodiment 96

The composition of Embodiment 95 wherein component (d) (i.e., the one or more inert formulating ingredients other than acrylate/methacrylate-based diblock copolymers) is at least about 0.1% of the composition by weight.

Embodiment 97

The composition of Embodiment 95 or 96 wherein component (d) is not more than about 20% of the composition by weight.

Embodiment 98

The composition of any one of Embodiments 95 through 97 wherein component (d) comprises at least one inert formulating ingredient selected from the group consisting of adhesives, liquid diluents, solid diluents, surfactants, antifreeze agents, preservatives, thickening agents and fertilizers.

Embodiment 99

The geotropic propagule described in the Summary of the Invention which is coated with an insecticidally effective amount of the composition of any one of Embodiments 1 through 98.

Embodiment 100

The geotropic propagule of Embodiment 99 which is a seed.

Embodiment 101

The seed of Embodiment 100 which is a seed of cotton, maize, soybean, rapeseed or rice.

Embodiment 102

The seed of Embodiment 101 which is a seed of maize or rapeseed.

Embodiment 103

The seed of Embodiment 102 which is a seed of maize.

Embodiment 104

The seed of Embodiment 102 which is a seed of rapeseed.

Embodiment 105

The liquid composition described in the Summary of the Invention consisting of about 5 to 80 weight % of the composition of any one of Embodiments 1 through 98 and about 20 to 95 weight % of a volatile aqueous liquid carrier.

Embodiment 106

The liquid composition of Embodiment 105 wherein the volatile aqueous liquid carrier is at least about 25% of the composition by weight.

Embodiment 107

The liquid composition of Embodiment 106 wherein the volatile aqueous liquid carrier is at least about 30% of the composition by weight.

Embodiment 108

The liquid composition of any one of Embodiments 105 through 107 wherein the aqueous liquid carrier is not more than about 70% of the composition by weight.

Embodiment 109

The liquid composition of any one of Embodiments 105 through 107 wherein the volatile aqueous liquid carrier comprises at least about 80% water by weight.

Embodiment 110

The liquid composition of Embodiment 109 wherein the volatile aqueous liquid carrier comprises at least about 90% water by weight.

Embodiment 111

The liquid composition of Embodiment 110 wherein the volatile aqueous liquid carrier comprises at least about 95% water by weight.

Embodiment 112

The liquid composition of Embodiment 111 wherein the volatile aqueous liquid carrier consists essentially of water.

Embodiment 113

The liquid composition of Embodiment 112 wherein the volatile aqueous liquid carrier is water.

Embodiment 114

The liquid composition of any one of Embodiments 105 through 113 wherein at least some of component (a) is present in the liquid composition as solid particles.

Embodiment 115

The liquid composition of Embodiment 114 wherein at least about 90% of component (a) is present in the composition as solid particles.

Embodiment 116

The liquid composition of Embodiment 115 wherein at least about 95% of component (a) is present in the composition as solid particles.

Embodiment 117

The liquid composition of Embodiment 116 wherein at least about 98% of component (a) is present in the composition as solid particles.

Embodiment 118

The liquid composition of any one of Embodiments 114 through 117 wherein more than 95% by weight of the particles have a particle size less than about 10 microns.

Embodiment 119

The liquid composition of any one of Embodiments 114 through 118 wherein the median particle size of the particles is not more than about 10 microns.

Embodiment 120

The liquid composition of Embodiment 118 or 119 wherein the median particle size of the particles is not more than about 4 microns.

Embodiment 121

The liquid composition of Embodiment 120 wherein the median particle size of the particles is not more than about 3 microns.

Embodiment 122

The liquid composition of Embodiment 121 wherein the median particle size of the particles in not more than about 2 microns.

Embodiment 123

The liquid composition of Embodiment 122 wherein the median particle size of the particles is not more than about 1 micron.

Embodiment 124

The liquid composition of any one of Embodiments 114 through 123 wherein the median particle size of the particles is at least about 0.1 micron.

Embodiment 125

The method described in the Summary of the Invention for protecting a geotropic propagule and plant derived therefrom from a phytophagous insect pest, the method comprising coating the propagule with an insecticidally effective amount of the liquid composition of any one of Embodiments 105 through 124 and then evaporating the volatile aqueous liquid carrier.

Embodiment 126

The method of Embodiment 125 wherein the insect pest is in a taxonomic order selected from Hemiptera and Lepidoptera.

Embodiment 127

The method of Embodiment 126 wherein the insect pest is in a taxonomic family selected from Aleyrodidae, Aphidadae, Cicadellidae, Delphacidae, Gelechiidae, Lymantriidae, Noctuidae, Plutellidae, Pyralidae and Torticidae.

Embodiment 128

The method of Embodiment 127 wherein the insect pest is in the family Noctuidae.

Embodiment 129

The composition of any one of Embodiments 1 through 98, wherein the acrylate/methacrylate-based diblock copolymer comprises at least one copolymer of Formula 2

2

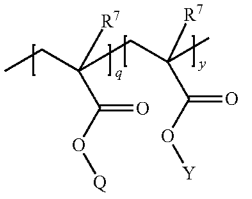

where each $R^7$ is independently selected from H and $CH_3$; and q and y are independently selected from integers from 5 to 600;

Q is benzyl, glycidyl, $C_1$-$C_{20}$ straight chain alkyl, (e.g., methyl, ethyl, n-butyl, hexadecyl, octadecyl, lauryl, stearyl), $C_3$-$C_{20}$ branched alkyl (e.g., isodecyl, isooctyl, isotridecyl, tert-butyl), 2-phenoxyethyl, isobornyl or tetrahydro furfuryl, or Q is a functional group derived from the reaction of a glycidyl group with cysteine, tryptophan, dihydroxyphenylalanine, or phenylalanine; and Y is hydroxyethyl or 3-hydroxy propyl, or Y is a functional group derived from the reaction of a glycidyl group with lysine, histidine, arginine, asparagine, glutamine, diethylene glycol, triethylene glycol, tetraethylene glycol, or 1,6-hexanediol, or Y is methoxy ethylene glycol polymers or ethylene glycol polymers with a degree of polymerization of 1 to 113.

Embodiment 130

The composition of Embodiment 129, wherein Q is methyl or benzyl and Y is $—(CH_2CH_2O)_2—H$, $—(CH_2CH_2O)_9—H$, or $—(CH_2CH_2O)_{30}—H$.

Embodiments of this invention can be combined in any manner. An example of such combination is the insecticidal composition described in the Summary of the Invention comprising by weight (a) from about 9 to about 91% of one or more anthranilic diamide insecticides; and (b) from about 9 to about 91% of an acrylate/methacrylate-based diblock copolymer component having a water solubility of at least about 5% by weight at 20° C., an HLB value ranging from about 3 to about 31 and an average molecular weight ranging from about 5,000 to about 35,000 daltons; wherein the ratio of component (b) to component (a) is about 1:5 to about 5:1 by weight.

Without further elaboration, it is believed that one skilled in the art using the preceding description can utilize the present invention to its fullest extent. The following Examples are, therefore, to be construed as merely illustrative and not limiting of the disclosure in any way whatsoever.

EXAMPLES

Table 1 describes the acrylate/methacrylate-based diblock copolymers used in the Examples and Comparative Examples. All acrylate/methacrylate-based diblock copolymers were synthesized as described below. Molecular weight and HLB values for the acrylate/methacrylate-based diblock copolymers were determined by SEC.

TABLE 1

Identity of Acrylate/methacrylate-based Diblock Copolymers

| Abbreviated Name | Formula 2 | MW (daltons) | HLB |
|---|---|---|---|
| 4-D165 | Q = $-CH_3$; Y = $-(CH_2CH_2O)_2-H$ | 13,968 | 13 |
| 4-D223 | Q = $-CH_3$; Y = $-(CH_2CH_2O)_2-H$ | 10,382 | 7 |
| 4-D291 | Q = $-CH_3$; Y = $-(CH_2CH_2O)_2-H$ | 10,362 | 3 |
| 5-D163 | Q = $-CH_3$; Y = $-(CH_2CH_2O)_9-H$ | 12,200 | 12 |
| 5-D221 | Q = $-CH_3$; Y = $-(CH_2CH_2O)_9-H$ | 9,900 | 7 |
| 5-D295 | Q = $-CH_3$; Y = $-(CH_2CH_2O)_9-H$ | 30,450 | 14 |
| 6-D161 | Q = $-CH_3$; Y = $-(CH_2CH_2O)_{30}-H$ | 10,560 | 11 |
| 6-D225 | Q = $-CH_3$; Y = $-(CH_2CH_2O)_{30}-H$ | 46,200 | 17 |
| 6-D293 | Q = $-CH_3$; Y = $-(CH_2CH_2O)_{30}-H$ | 45,540 | 16 |

PCT Patent Publication WO 2006/062978 discloses methods for preparing 3-bromo-1-(3-chloro-2-pyridinyl)-N-[4-cyano-2-methyl-6-[(methylamino)carbonyl]phenyl]-1H-pyrazole-5-carboxamide (i.e., Compound 1). Example 15 of this publication discloses preparation of Compound 1 as a powder melting at 177-181° C. (with apparent decomposition), which is a crystal form that is readily hydrated. Example 15 also discloses recrystallization from 1-propanol to provide crystals melting at 217-219° C., which is an anhydrous crystal form that is resistant to hydration. The samples of Compound 1 used in the present Examples and Comparative Examples were assayed to contain about 94-98% by weight of Compound 1, which is believed to be a mixture of these two crystal forms.

PCT Patent Publication WO 03/015519 discloses methods for preparing 3-bromo-N-[4-chloro-2-methyl-6-[(methylamino)carbonyl]phenyl]-1-(3-chloro-2-pyridinyl)-1H-pyrazole-5-carboxamide (i.e., Compound 2). Example 7 of this publication discloses preparation of Compound 2 as a powder melting at 239-240° C. The samples of Compound 2 used in the present Examples and Comparative Examples were assayed to contain about 96-97% by weight of Compound 2.

The weight percentages of Compound 1 or 2 reported in the present Examples refer to the amount of Compound 1 or 2 contained in the technical material used; the other constituents in the technical material are not separately listed, but when added to weight percentages of the listed composition components result in a total of about 100%.

General Procedure for Coating Seeds

A fluidized bed system was used for coating seeds with the compositions described in the following examples. Seeds were tossed by vertical streams of hot air while being sprayed with the aqueous composition. The hot air evaporated the water carrier from the composition applied to the seeds. The amount of composition introduced into the coating system was adjusted to compensate for material lost exiting the coater or coating areas other than the seeds, so as to deliver the stated target application rate to the seeds.

General Procedure for Assaying Anthranilic Diamide Concentration in Leaves

Plant leaves were macerated using a Geno/Grinder 2000 bead beater homogenizer (SPEX CertiPrep, Metuchen, N.J., USA), and then acetonitrile (~5 mL/g of leaf tissue) was added. The mixture was further shaken for 1 minute using the Geno/Grinder homogenizer, and then centrifuged. The acetonitrile extract supernatant was analyzed by high performance liquid chromatography with tandem mass spectrometry detection (HPLC/MS/MS) using a Waters (Milford, Mass. USA) Alliance HT2795 chromatograph and Zorbax SB C18 (2.1×50 mm, 5 micron) column eluted with mixtures of water and acetonitrile containing 0.1% (volume/volume) of formic acid, with detection by a Waters Quattro Micro API Mass Spectrometer using electrospray ionization (ESI+). Standard solutions of Compound 1 and Compound 2 were prepared by adding measured amounts of stock solutions of Compound 1 or Compound 2 in acetonitrile or tetrahydrofuran to acetonitrile extracts of leaves from plants grown from untreated seeds.

In a laboratory test involving 2nd instar larva of *Spodoptera frugiperda* on maize leaves, a concentration of 0.033 micrograms of Compound 2 per g of leaf tissue resulted in 50% mortality within 72 h, and a concentration of 0.037 micrograms per g of tissue was needed to achieve 100% mortality within 72 h.

Examples 1-9

Synthesis and Purification

Monomer Purification

Acrylate/methacrylate-based monomers (e.g., Aldrich M55909) were filtered through a 20 cm long, 2 cm diameter column filled with 6 cm of Alumina Basic (Dynamic Adsorbents, Inc. 02078-1).

Copper Purification

VWR Glass Vials (66012-022) were charged with copper (I) bromide (2 g; Aldrich 254185). Glacial acetic acid was added (20 mL) and the contents of the vial were stirred for 4 hrs at room temperature. The contents of the vial were filtered and washed with 50 mL ethanol three times, followed by 3 washes with 50 mL ether, followed by drying at 60° C. overnight in a vacuum oven.

Polymer Synthesis

Glass vials, ground glass plunger syringes, stainless steel plunger syringes, and 10 mm Teflon stir bars were dried in an oven set at 200° C. for 12 hours. The materials were removed and pumped under vacuum through the antechamber port to 0.05 torr of a nitrogen atmosphere dry box for 1 hr. The vial was charged with purified Cu(I)Br (0.037 g; 0.009 moles) and 2,2'-bipyridine (0.118 g), followed by syringe addition of tetrahydrofuran (10 mL), followed by syringe addition of Monomer 1. The vial was placed on a heating plate with PIE Block safety holder (CG-1991-P-05) equipped with 4-place pie wedge for 20 mL scintillation vials, with IKA ETS-D4 fuzzy thermocouple set to 60° C. for 10 minutes. Initiator (ethyl 2-bromoisobutyrate) was added and the vial was capped. After 6 hrs, an aliquot was taken (100 microliter) for Gel Permeation Chromatography (GPC) analysis, followed by syringe addition of distilled Monomer 2 (methyl methacrylate). After 12 hrs, an aliquot was taken (100 microliter) for GPC analysis. The polymer was then removed from the nitrogen atmosphere box and purified by diluting to a 1% (w/v) solution in THF, followed by passage through a 20 cm long, 2 cm diameter column filled with 6 cm of basic alumina with a THF mobile phase. The solvent from the collected polymer solution was removed by a rotary evaporator fixed with a dry ice/acetone trap. Descriptions of the acrylate/methacrylate-based diblock copolymers synthesized are shown in Table 2.

TABLE 2

Synthesis of Acrylate/methacrylate-based Diblock Copolymers

| Abbreviated Name | Initiator (moles) | Monomer 1 (moles) | Monomer 2 (moles) | MW (daltons) |
|---|---|---|---|---|
| 4-D165 | 0.0001 | Y = —$(CH_2CH_2O)_2$—H (0.005) | methyl methacrylate (0.005) | 13,968 |
| 4-D223 | 0.00007 | Y = —$(CH_2CH_2O)_2$—H (0.003) | methyl methacrylate (0.007) | 10,382 |
| 4-D291 | 0.00006 | Y = —$(CH_2CH_2O)_2$—H (0.001) | methyl methacrylate (0.009) | 10,362 |
| 5-D163 | 0.0001 | Y = —$(CH_2CH_2O)_9$—H (0.003) | methyl methacrylate (0.007) | 12,200 |
| 5-D221 | 0.00007 | Y = —$(CH_2CH_2O)_9$—H (0.001) | methyl methacrylate (0.009) | 9,900 |
| 5-D295 | 0.00006 | Y = —$(CH_2CH_2O)_9$—H (0.005) | methyl methacrylate (0.005) | 30,450 |
| 6-D161 | 0.0001 | Y = —$(CH_2CH_2O)_{30}$—H (0.001) | methyl methacrylate (0.009) | 10,560 |
| 6-D225 | 0.00007 | Y = —$(CH_2CH_2O)_{30}$—H (0.005) | methyl methacrylate (0.005) | 46,200 |
| 6-D293 | 0.00006 | Y = —$(CH_2CH_2O)_{30}$—H (0.003) | methyl methacrylate (0.007) | 45,540 |

Y group —$(CH_2CH_2O)_2$—H is referred to as -(methoxy) ethoxy ethyl; Y group —$(CH_2CH_2O)_9$—H is referred to as oligomethoxyethylene glycol; Y group —$(CH_2CH_2O)_{30}$—H is referred to as poly(methoxy ethylene glycol)$_{30}$.

Examples 1-9 and Comparative Example A

Description of Examples from Canola Greenhouse Trials

General Procedure for Preparing Insecticidal Compositions

For Examples 1 to 9, 0.5 g of acrylate/methacrylate-based diblock and 0.51 g of Compound 1 were dissolved in 50 mL of 30 wt % ethanol/methylene chloride. The solvent was removed by rotary evaporation. Some of the residue (0.5 g) was mixed with 1 g of water for seed coating.

The compositions of Examples 1-9 and Comparative Example A were mixed with a 1:3 by weight mixture of the fungicide products MAXIM 4FS (40.3% fludioxonil, syngenta AG) and APRON XL (33.3% mefenoxam, Syngenta AG), and (2) the colorant Acid Blue 1 dye (Simpsons (UK Ltd)), and then the resultant compositions were used to coat canola seeds at an application rate of 0.6 g of Compound 1, 0.067 mL of the fungicide mixture (1A) and 0.033 g of the colorant (2) per 100 g of canola seeds (100 g corresponding to about 23,400 seeds for Examples 1-9, and Comparative Example A). ("Canola" is a cultivar of the rapeseed species *Brassica napus* L. that produces an edible oil.)

For Comparative Example A, 1.01 g of Compound 1 was dissolved in 50 mL of 30 wt % ethanol/methylene chloride. The solvent was removed by rotary evaporation. Some of the residue (0.5 g) was mixed with 1 g of water for seed coating.

The coated canola seeds were then evaluated for ability to provide Compound 1 to leaves developing from the seeds. Each treatment involved four pots to provide quadruple replication. Four coated canola seeds were planted in sterile Matapeake sand blend soil in each pot and then grown in a growth chamber (25° C., 18 h light, 6 h dark) for 18-20 days. Three plants in each pot were selected for sampling. From each of the three plants, the second leaf was cut at the stem. All three leaves collected from each pot were placed into one vial and then analyzed according to the general procedure described above for assaying anthranilic diamide concentration in leaves. The concentrations measured from leaves in each of the four pots (total of 12 leaves) were averaged to provide the values reported in Table 3.

TABLE 3

Uptake of Compound 1 in Canola

| | Component (b) | MW (daltons) | HLB | Uptake ug/g of leaf | Normalized Improvement vs Compound 1* |
|---|---|---|---|---|---|
| Example | | | | | |
| 1 | 4-D165 | 13,968 | 13 | 0.054 | 4.9 |
| 2 | 4-D223 | 10,382 | 7 | 0.076 | 6.9 |
| 3 | 4-D291 | 10,362 | 3 | 0.045 | 4.1 |
| 4 | 5-D163 | 12,200 | 12 | 0.095 | 8.6 |
| 5 | 5-D221 | 9,900 | 7 | 0.044 | 4 |
| 6 | 5-D295 | 30,450 | 14 | 0.058 | 5.3 |
| 7 | 6-D161 | 10,560 | 11 | 0.041 | 3.7 |
| 8 | 6-D225 | 46,200 | 17 | 0.055 | 5 |
| 9 | 6-D293 | 45,540 | 16 | 0.068 | 6.2 |
| Comparative Example | | | | | |
| A | Compound 1 | | NA | 0.011 | 1 |

*The "Improvement vs Compound 1" represents the amount of Compound 1 taken up by the leaves in the presence of component (b) divided by the amount of Compound 1 taken up in the absence of component (b).

Examples 10-12 and Comparative Example B

Greenhouse Results for Corn and Compound 2

For corn and Compound 2, a 1:1 weight ratio mixture of acrylate/methacrylate-based diblock copolymers with Compound 2 was prepared with each additive by mixing the appropriate amount of either 16.7 wt % or 20.0 wt % solution in water of the acrylate/methacrylate-based diblock copolymers with 1.0 g of Compound 2. For Comparative Example B, 1.01 g of Compound 2 was dissolved in 50 mL of 30 wt % ethanol/methylene chloride. The solvent was removed by rotary evaporation. Some of the residue (0.5 g) was mixed with 1 g of water for seed coating.

These mixtures were used to coat field corn seeds at 100 g/seed (100 g corresponding to about 281 seeds for Examples 10-12 and Comparative Example B). The corn seeds were planted and third leaf was collected for analyses similar to the procedure used for canola and Compound 1. The uptake of Compound 2 is shown in Table 4.

TABLE 4

Uptake of Compound 2 in Corn

| | Component (b) | MW (daltons) | HLB | Uptake ug/g of leaf | Improvement vs Compound 2* |
|---|---|---|---|---|---|
| Example | | | | | |
| 10 | 5-D295 | 30,450 | 14 | 0.39 | 1.1 |
| 11 | 6-D293 | 45,540 | 16 | 0.38 | 1.1 |
| 12 | 6-D225 | 46,200 | 17 | 0.44 | 1.2 |
| Comparative Example | | | | | |
| B | Compound 2 | 373 | NA | 0.35 | 1.0 |

*The "Improvement vs Compound 2" represents the amount of Compound 2 taken up by the leaves in the presence of component (b) divided by the amount of Compound 2 taken up in the absence of component (b).

What is claimed is:

1. An insecticidal composition comprising by weight based on the total weight of the composition:

(a) from about 9 to about 91% of one or more anthranilic diamide insecticides; and (b) from about 9 to about 91% of an acrylate/methacrylate-based diblock copolymer component having a water solubility of at least 5% by weight at 20° C., a hydrophilic-lipophilic balance value of at least 3 and not more than 35, and an average molecular weight ranging from about 1,500 to about 50,000 Daltons;

wherein component (a) comprises at least one compound selected from anthranilic diamides of Formula 1, N-oxides, and salts thereof,

1

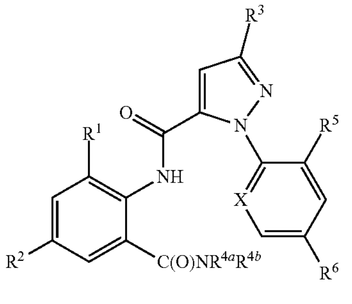

wherein

X is N;

R1 is $CH_3$, Cl, Br or F;

R2 is H, F, Cl, Br or —CN;

R3 is F, Cl, Br, C1-C4 haloalkyl or C1-C4 haloalkoxy;

R4a is H, C1-C4 alkyl, cyclopropylmethyl or 1-cyclopropylethyl;

R4b is H or $CH_3$;

R5 is H, F, Cl or Br; and

R6 is H, F, Cl or Br, wherein component (b) is selected from acrylate/methacrylate-based diblock copolymers of Formula 2,

2

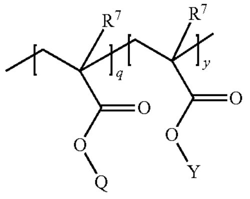

where each $R^7$ is independently selected from H and $CH_3$;

$5 \leq q \leq 600$;

$5 \leq y \leq 600$;

Q is $C_1$-$C_{20}$ straight chain alkyl or $C_3$-$C_{20}$ branched alkyl; and Y is hydroxyethyl or 3-hydroxy propyl, or Y is $-(CH_2CH_2O)_2-H$, $-(CH_2CH_2O)_9-H$, or $-(CH_2CH_2O)_{30}-H$, and wherein the ratio of component (b) to component (a) is about 1:10 to about 10:1 by weight.

2. The composition of claim 1, wherein component (a) is selected from compounds of Formula 1 wherein X is N; $R^1$ is $CH_3$; $R^2$ is Cl or —CN; $R^3$ is Br; $R^{4a}$ is $CH_3$; $R^{4b}$ is H; $R^5$ is Cl; and $R^6$ is H; and salts thereof.

3. The composition of claim 1, wherein component (a) is the compound of Formula 1 wherein $R^2$ is Cl.

4. The composition of claim 2, wherein component (a) is the compound of Formula 1 wherein $R^2$ is —CN.

5. The composition of claim 1, wherein component (b) is at least 15% of the composition by weight.

6. The composition of claim 1, wherein the ratio of component (b) to component (a) is at least 1:5 by weight.

7. The composition of claim 1, further comprising at least one fungicide or insecticide other than anthranilic diamide insecticides.

8. A geotropic propagule coated with an insecticidally effective amount of the composition of claim 1.

9. The composition of claim 8, wherein the geotropic propagule is a seed.

10. The composition of claim 9, wherein the seed is a seed of cotton, maize, soybean, rapeseed or rice.

11. A liquid composition consisting of about 5 to 80 weight % of the composition of claim 1 and about 20 to 95 weight % of a volatile aqueous liquid carrier.

12. A method for protecting a geotropic propagule and plant derived therefrom from a phytophagous insect pest, the method comprising coating the propagule with an insecticidally effective amount of the liquid composition of claim 11 and then evaporating the volatile aqueous liquid carrier of the composition.

13. The method of claim 12 wherein the insect pest is in a taxonomic order selected from Hemiptera and Lepidoptera.

* * * * *